(12) United States Patent
Kim et al.

(10) Patent No.: US 9,795,586 B2
(45) Date of Patent: Oct. 24, 2017

(54) HNF4-α ANTAGONIST AND USE THEREOF

(71) Applicant: NATIONAL CANCER CENTER, Goyang-si (KR)

(72) Inventors: Yon Hui Kim, Seoul (KR); Seung Yoon Nam, Seoul (KR); Hee Seo Park, Dongducheon-si (KR); Hae Ryung Chang, Seoul (KR); Hae Rim Jung, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 15/464,178

(22) Filed: Mar. 20, 2017

(65) Prior Publication Data
US 2017/0189371 A1 Jul. 6, 2017

Related U.S. Application Data

(62) Division of application No. 14/988,124, filed on Jan. 5, 2016.

(30) Foreign Application Priority Data

Jan. 5, 2015 (KR) .................. 10-2015-0000759
Jan. 5, 2016 (KR) .................. 10-2016-0000813

(51) Int. Cl.
*A61K 31/343* (2006.01)
(52) U.S. Cl.
CPC .................. *A61K 31/343* (2013.01)

(58) Field of Classification Search
None
See application file for complete search history.

(56) References Cited

U.S. PATENT DOCUMENTS

2010/0286220 A1  11/2010  Levine et al.

FOREIGN PATENT DOCUMENTS

| JP | 2008-133247 A | 6/2008 |
| WO | 02/24227 A1 | 3/2002 |

OTHER PUBLICATIONS

STN Registry RN 556830-41-2, "Benzoic acid, 4-chloro-3-nitro, 2-dibenzofuranyl ester," entered Jul. 29, 2003, 1 page.

*Primary Examiner* — Bong-Sook Baek
(74) *Attorney, Agent, or Firm* — Seed IP Law Group LLP

(57) ABSTRACT

Provided is a hepatocyte nuclear factor 4 alpha (HNF4-α) antagonist and a use thereof. The HNF4-α antagonist selected in the present invention was confirmed to specifically bind to the ligand binding domain of HNF4-α, thereby inhibiting the activity of HNF4-α. The HNF4-α antagonist of the present invention can significantly reduce the expression of Wnt5a in a specific manner compared to that of the conventional known HNF4-α antagonists, and can also inhibit the growth of gastric cancer cells. Therefore, the HNF4-α antagonist of the present invention can not only be used as a pharmaceutical composition or a health functional food for preventing and treating cancer but can also be applied to a composition for treating or preventing diseases occurring due to the overexpression of HNF4-α.

3 Claims, 13 Drawing Sheets

HNF4-α ANTAGONIST AND USE THEREOF

CROSS-REFERENCE TO RELATED APPLICATIONS

This U.S. non-provisional patent application is a divisional of U.S. non-provisional patent application Ser. No. 14/988,124, filed on Jan. 5, 2016, which claims priority under 35 U.S.C. §119 of Korean Patent Application No. 10-2015-0000759, filed on Jan. 5, 2015, and Korean Patent Application No. 10-2016-0000813, filed on Jan. 5, 2016, the entire contents of which are hereby incorporated by reference.

BACKGROUND OF THE INVENTION

The present invention disclosed herein relates to a hepatocyte nuclear factor 4 alpha (HNF4-α) antagonist and a use thereof, and more specifically, to an antagonist which specifically binds to the ligand binding domain of HNF4-α and inhibits the activity of HNF4-α, and a composition which includes the HNF4-α antagonist as an active ingredient and is for preventing and treating gastric cancer.

Hepatocyte nuclear factor 4 alpha (HNF4-α), being a hepatocyte nuclear factor, is a DNA binding protein which is present in nuclei, abundant in the liver, and known as a transcription factor involved in the control of liver-specific genes. Additionally, HNF4-α is a transcription factor belonging to a steroid receptor family and activates the HNF1-α gene. Although it was reported in a previous study that HNF4-α activates the transcription of a target gene in the non-presence of an exogenous ligand, a later study revealed that a particular fatty acid acyl-CoA activates HNF4-α, thereby controlling the activity of HNF4-α by a particular ligand.

Additionally, it is known that HNF4-α indeed controls the expression of the genes associated with lipid transport, such as microsomal triglyceride transfer protein (MTP), apolipoprotein B (apoB), and apolipoprotein CIII (apoCIII), or the expression of genes associated with glucose metabolism, such as phosphenolpyruvate carboxykinase (PEPCK) and glucose-6-phosphatase (G6Pase). HNF4-α is expressed in the kidneys and intestines as well as in the liver, and is widely associated with energy metabolism in vivo or maintenance of homeostasis, such as synthesis, transport, and secretion of fatty acids and regulation of cell cycle.

HNF4-α is known to control not only the transcription of genes necessary in the processes of metabolism of cholesterol, fatty acids, and glucose and decomposition in the liver, but also the transcription of representative drug-metabolizing enzymes, such as cytochrome P450 2D6 (CYP2D6), cytochrome P450 2B6 (CYP2B6), cytochrome P450 3A4 (CYP3A4), and cytochrome P450 2C9 (CYP2C9).

In fact, it has been acknowledged in mice with the deletion of HNF4-α that there are reductions in the expression of MTP and apo proteins, reduction of serum cholesterol and serum triglycerides in the liver, and reduction in body weight. Therefore, it has been speculated that inhibiting the activity of HNF4-α may render the capabilities of controlling lipid metabolism and glucose metabolism, and may be effectively used to develop an agent for preventing or improving hypertriglyceridemia, fatty liver, and diabetes.

In the conventional art, it was reported that the transcription activity of HNF4-α is inhibited by small heterodimer partner (SHP), which is one of the target proteins of farnesoid X receptor (FXR), and as ligands acting on the HNF4a protein, long-chain fatty acid acyl CoA (palmitoyl CoA, myristoyl-CoA, dodecanoyl-CoA, stearoyl-CoA, linoleoyl-CoA, liolenoyl CoA, eicosapentaenoyl-CoA, docosahexaenoyl-CoA) has been reported.

Japanese Patent Application Publication No. 2008-133247 discloses nitrogenistein, which is an inhibitor of HNF4-α activity for preventing or improving fatty liver or diabetes, International Patent Publication No. WO2002-024227 discloses that HNF4α protein is overexpressed in colorectal tissues and that inhibiting HNF4α protein can inhibit the proliferation of tumor cells, and U.S. Patent Application Publication No. 2010-0286220 discloses the BIM5078 compound as a HNF4-α antagonist.

Meanwhile, gastric cancer, being a malignant tumor occurring in the stomach, includes gastric adenocarcinoma developing on the epithelium of the stomach, a malignant lymphoma developing on the submucosa, myosarcoma, interstitial tumor, etc., but generally refers to gastric adenocarcinoma.

Gastric adeno-carcinoma is the second leading cause of cancer-related death among 700,349 deaths in 2000, and is the fourth most commonly diagnosed cancer in the world. Gastric adeno-carcinoma is considered a single heterogeneous disease having several epidemiological and pathological characteristics. Gastric cancer treatment is based on clinical parameters, such as tumor, node, and metastasis (TNM) staging which determines whether patients should be treated by surgery only or by surgery and chemotherapy. Gastric cancer stage, unlike other cancers such as breast cancer and colorectal cancer, can be clearly distinguished from stage I to stage IV according to the TNM staging system. That is, the survival rate of patients with stage I gastric cancer is 90% or more, while those with stage IV gastric cancer is 20% or less, thus showing a big difference. Based on the staging system described above, gastric cancer can be classified into early gastric cancer, locally advanced gastric cancer, locally advanced invasive gastric cancer, or metastatic gastric cancer, etc.

The present inventors have confirmed through previous studies that HNF4-α is overexpressed in an early stage of gastric cancer to thereby increase the expression of Wnt5α, and have also confirmed that when shRNA is used to inhibit the expression of the HNF4-α gene, or the HNF4-α antagonist is treated, the formation of tumors can be inhibited by controlling the Wnt signal.

Accordingly, while endeavoring to select HNF4-α antagonists for preventing and treating gastric cancer, the present inventors have selected the compounds which can inhibit the activity of HNF4-α by specifically binding to the HNF4-α of the ligand binding domain, and have confirmed that the selected compounds can specifically reduce the expression of Wnt5a and significantly inhibit the growth of gastric cancer, thereby completing the invention.

SUMMARY OF THE INVENTION

Being contrived to solve the limitations described above, an object of the present invention is to provide an HNF4-α antagonist which specifically binds to the ligand binding domain of HNF4-α and inhibits the activity of HNF4-α, and a pharmaceutical composition which is for preventing and treating gastric cancer and includes the HNF4-α antagonist as an active ingredient.

To achieve the above objects, the present invention provides a hepatocyte nuclear factor 4 alpha (HNF4-α) antagonist including at least one selected from the group consisting of at least one type of a compound selected from the group consisting of the following Formula 1 and Formula 2; and salts thereof:

[Formula 1]

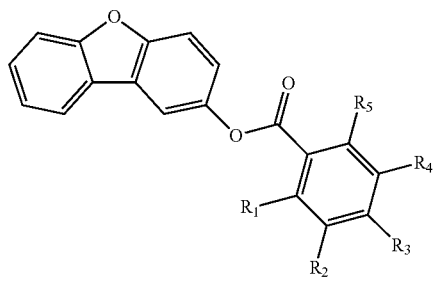

[Formula 2]

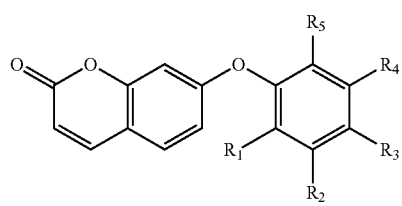

wherein $R_1$ to $R_5$ are each independently a hydrogen atom (H), an oxygen atom (O), a nitro group($NO_2$), a halogen atom, a $C_{1-6}$ alkyl group substituted with one to six identical or different halogen atoms, or a $C_{1-6}$ alkyl group.

In an exemplary embodiment of the present invention, Formula 1 may be expressed by the following Formula 3,

[Formula 3]

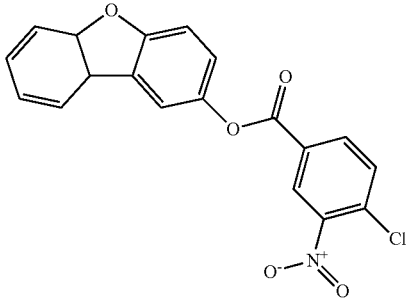

and Formula 2 may be expressed by the following Formula 4,

[Formula 4]

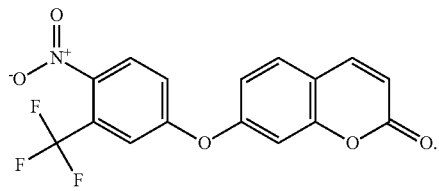

In another exemplary embodiment of the present invention, Formula 1 and Formula 2 can specifically bind o the ligand binding domain of HNF4-α.

The present invention also provides a hepatocyte nuclear factor 4 alpha (HNF4-α) antagonist including at least one type selected from the group consisting of at least one type of a compound selected from the group consisting of the following Formula 5 and Formulas 5-1 to 5-7, which are derivatives of Formula 5; and salts thereof.

[Formula 5]

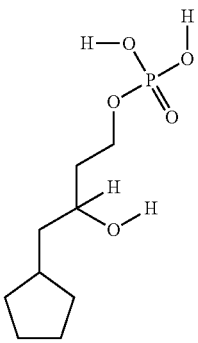

[Formula 5-1]

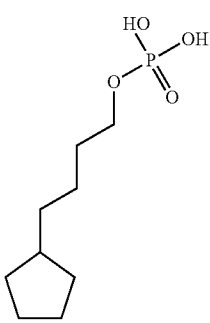

[Formula 5-2]

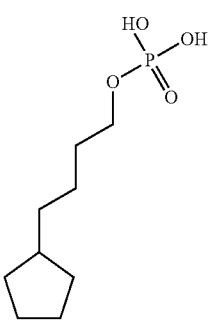

[Formula 5-3]

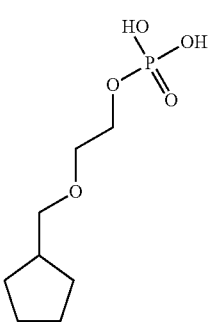

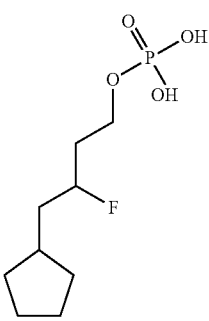

[Formula 5-4]

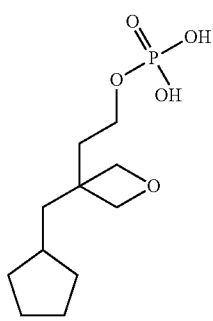

[Formula 5-5]

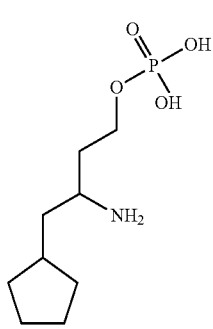

[Formula 5-6]

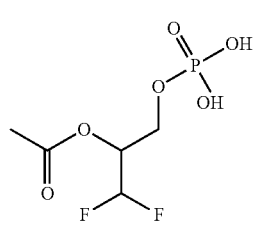

[Formula 5-7]

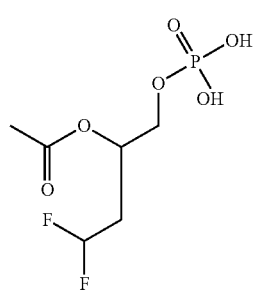

[Formula 6]

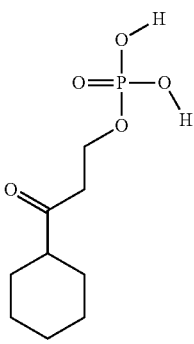

[Formula 6-1]

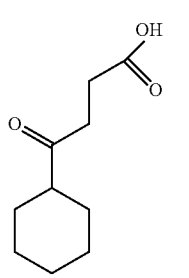

[Formula 6-2]

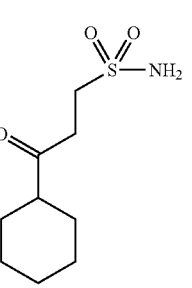

[Formula 6-3]

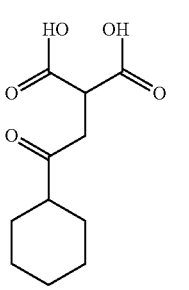

[Formula 6-4]

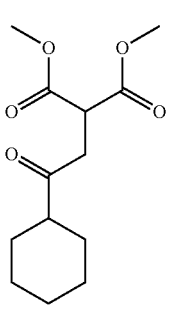

The present invention also provides a hepatocyte nuclear factor 4 alpha (HNF4-α) antagonist including at least one type selected from the group consisting of at least one type of a compound selected from the group consisting of the following Formula 6 and Formulas 6-1 to 6-10, which are derivatives of Formula 6; and salts thereof.

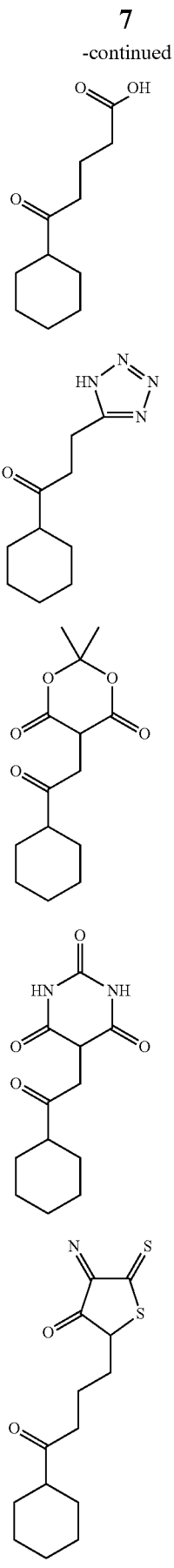
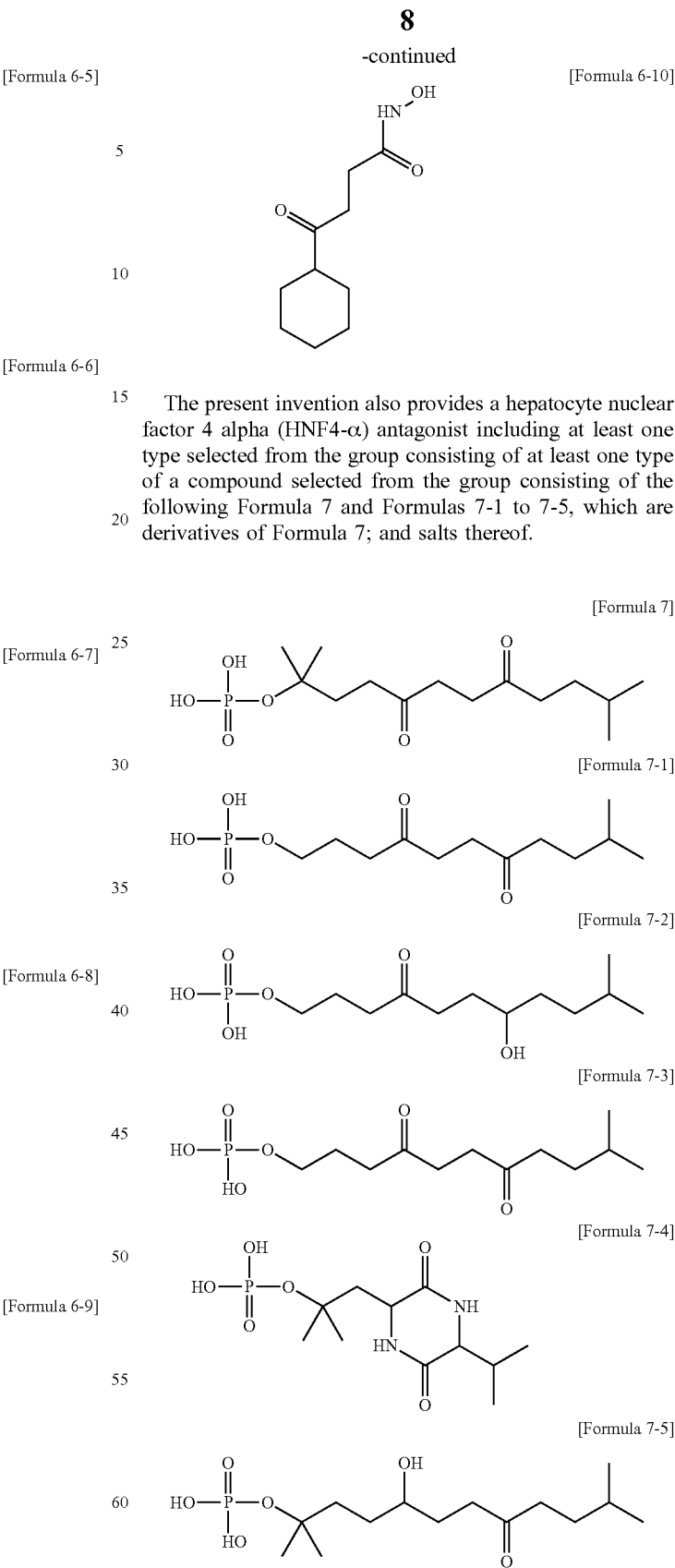

The present invention also provides a hepatocyte nuclear factor 4 alpha (HNF4-α) antagonist including at least one type selected from the group consisting of at least one type of a compound selected from the group consisting of the following Formula 7 and Formulas 7-1 to 7-5, which are derivatives of Formula 7; and salts thereof.

The present invention also provides a hepatocyte nuclear factor 4 alpha (HNF4-α) antagonist including at least one type selected from the group consisting of at least one type of a compound selected from the group consisting of the following Formula 8 and Formula 8-1, which is a derivative of Formula 8; and salts thereof.

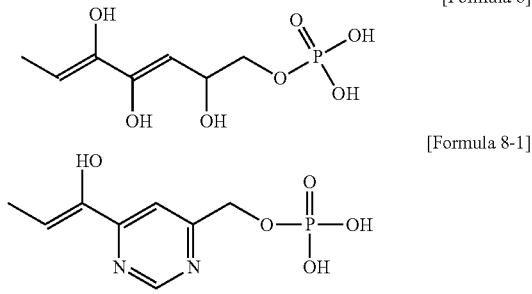

[Formula 8]

[Formula 8-1]

The present invention also provides a pharmaceutical composition for preventing and treating cancer including the HNF4-α antagonist as an active ingredient, and a health functional food for preventing and improving cancer including the HNF4-α antagonist as an active ingredient.

In still another exemplary embodiment of the present invention, the HNF4-α antagonist may reduce the expression of wingless-type MMTV integration site family, member 5A (Wnt5a) by inhibiting the activity of HNF4-α.

In still another exemplary embodiment of the present invention, the cancer may be at least one type selected from the group consisting of gastric cancer, colorectal cancer, breast cancer, cervical cancer, and liver cancer.

Advantageous Effects of the Invention

The present invention relates to a hepatocyte nuclear factor 4 alpha (HNF4-α) antagonist and a use thereof. The HNF4-α antagonist selected in the present invention was confirmed to specifically bind to the ligand binding domain of HNF4-α, thereby inhibiting the activity of HNF4-α. The HNF4-α antagonist of the present invention can significantly reduce the expression of Wnt5a in a specific manner compared to that of the conventional known HNF4-α antagonists, and also inhibit the growth of gastric cancer cells. Therefore, the HNF4-α antagonist of the present invention can not only be used as a pharmaceutical composition or a health functional food for preventing and treating cancer, but can also be applied to a composition for treating or preventing diseases occurring due to the overexpression of HNF4-α.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
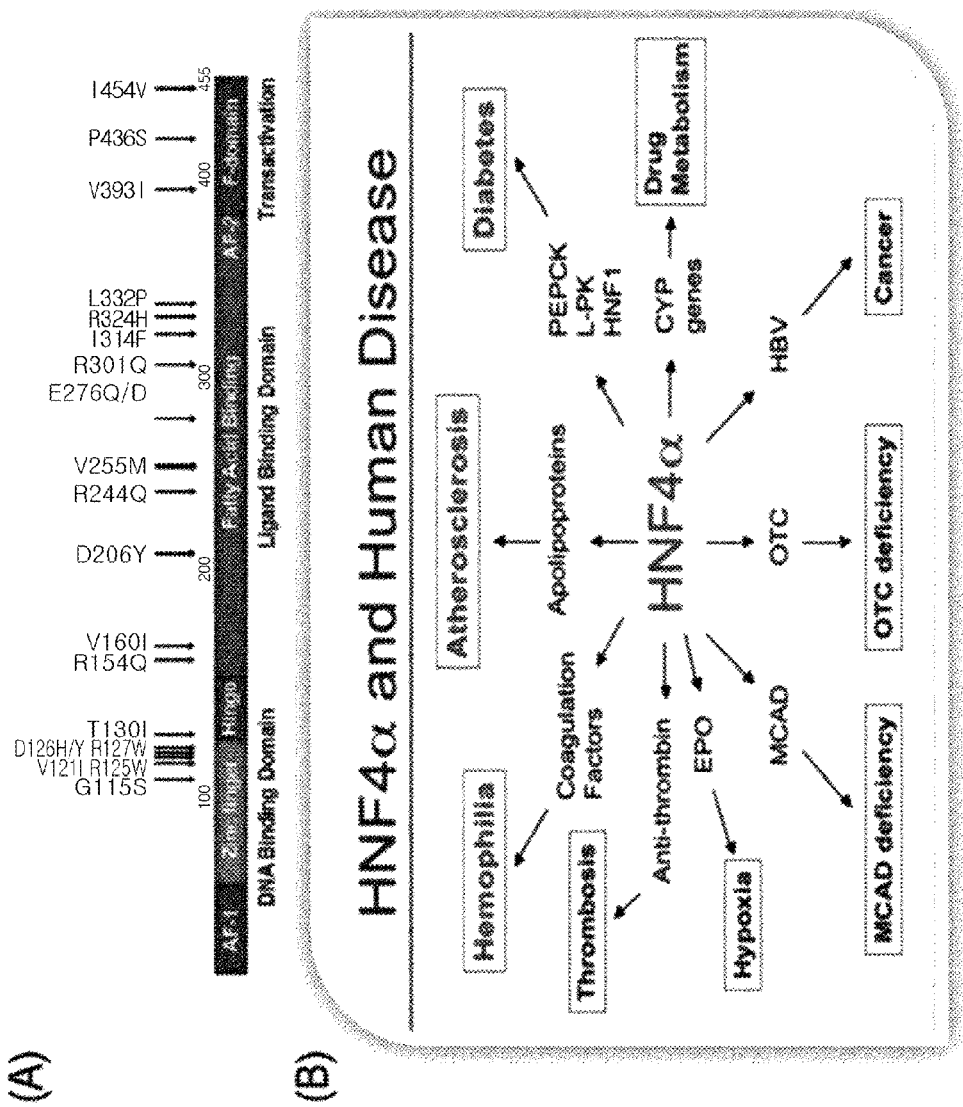
FIG. 1 is a schematic diagram illustrating the structure of HNF4-α (A) and a schematic diagram illustrating diseases that may occur due to the overexpression of HNF4-α.

Hereinafter, the present invention is described in more detail.

As described above, HNF4-α antagonists capable of inhibiting the activity of HNF4-α have been studied for the treatment of various diseases occurring due to the overexpression of HNF4-α, and the present inventors have discovered that inhibiting the activity of the overexpressed HNF4-α can inhibit tumorigenesis by controlling the Wnt signal, and have attempted to select HNF4-α antagonists for preventing and treating gastric cancer.

In this regard, the present inventors have attempted to solve the aforementioned limitations by providing a HNF4-α antagonist, which specifically binds to the ligand binding domain of HNF4-α and inhibits the activity of HNF4-α. Since, the expression of Wnt5a may thereby be significantly reduced in a specific manner compared to that of HNF4-α antagonists known previously and the growth of gastric cancer cells inhibited, a pharmaceutical composition or a health functional food which is for preventing and treating cancer and includes the HNF4-α antagonist may be provided.

Accordingly, the present invention provides a hepatocyte nuclear factor 4 alpha (HNF4-α) antagonist including at least one selected from the group consisting of at least one type of a compound selected from the group consisting of the following Formula 1 and Formula 2; and salts thereof:

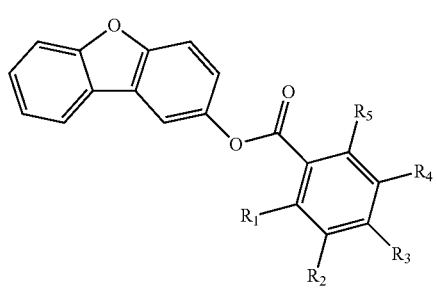

[Formula 1]

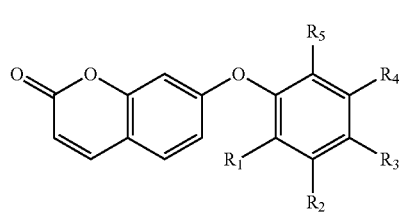

[Formula 2]

wherein $R_1$ to $R_5$ are each independently a hydrogen atom (H), an oxygen atom (O), a nitro group($NO_2$), a halogen atom, a $C_{1-6}$ alkyl group substituted with one to six identical or different halogen atoms, or a $C_{1-6}$ alkyl group.

The halogen atom may be, for example, at least one type of an atom selected from the group consisting of bromine (Br), chlorine (Cl), fluorine (F), and iodine (I); and the $C_{1-6}$ alkyl group, being a linear or branched saturated hydrocarbon having 1 to 6 carbon atoms, may be at least one type selected from the group consisting of methyl, ethyl, n-propyl, isopropyl, n-butyl, iso-butyl, sec-butyl, tert-butyl, n-pentyl, and n-hexyl groups.

The "$C_{1-6}$ alkyl group that can be substituted with one to six identical or different halogen atoms" is, in addition to the $C_{1-6}$ alkyl group, is a $C_{1-6}$ alkyl group substituted with one to three identical or different "halogen atoms" described above, such as trifluoromethyl group, trichloromethyl group, difluoromethyl group, dichloromethyl group, dibromomethyl group, fluoromethyl group, chloromethyl group, bromomethyl group, iodomethyl group, 2,2,2-trichloroethyl group, 2,2,2-trifluoroethyl group, 2-bromoethyl group, 2-chloroethyl group, 2-fluoroethyl group, 3-chloropropyl group, 3,3,3-trifluoropropyl group, 4-fluorobutyl group, 3-fluoro-2-methylpropyl group, 3,3,3-trifluoro-2-methylpropyl group, and 6,6,6-trichlorohexyl group; preferably "a $C_{1-4}$ alkyl group" that can be substituted with one to three identical or different "halogen atoms" described above; more preferably "a $C_{1-3}$ alkyl group" that can be substituted with one to three identical or different "fluorine atoms or chlorine atoms" described above; even more preferably a methyl group, an ethyl group, a propyl group, a chloromethyl group, or a trifluoromethyl group; and most preferably, a methyl group, an ethyl group, or a trifluoromethyl group.

Preferably, in Formula 1, $NO_2$ may be positioned in $R_2$ or $R_4$, or a halogen atom may be positioned in $R_3$, or more preferably, Formula 1 may be expressed by the following Formula 3.

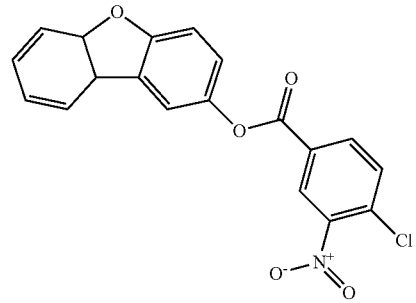

[Formula 3]

Preferably, in Formula 2, $NO_2$ may be positioned in $R_3$, or a $C_{1-6}$ alkyl group which can be substituted with one to six identical or different halogen atoms may be positioned in $R_2$ or $R_4$, or more preferably, Formula 4, may be expressed by the following Formula 4.

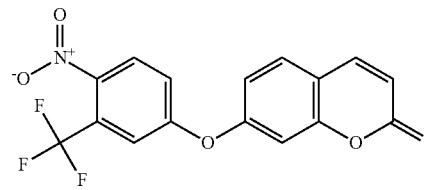

[Formula 4]

In the present invention, the HNF4-α antagonist expressed by Formula 1 and Formula 2, or the HNF4-α antagonist expressed by Formula 3 and Formula 4 may specifically bind to the ligand binding domain of HNF4-α, and the activity of HNF4-α can be inhibited by the binding.

As used herein, the term "hepatocyte nuclear factor 4 alpha (HNF4-α)" is known as a DNA binding protein that is present in the nucleus. FIG. 1A is a schematic diagram illustrating the structure of HNF4-α protein. The HNF4-α protein consists of a DNA binding domain, the ligand binding domain, and a transactivation domain, and the HNF4-α antagonist specifically binds to the ligand binding domain of HNF4-α and thereby inhibits the activity of HNF4-α.

FIG. 1B is a schematic diagram illustrating the diseases that may occur due to the overexpression of HNF4-α protein. HNF4-α is known to cause diseases such as diabetes, atherosclerosis, hemophilia, thrombosis, hypoxia, medium chain acyl-CoA dehydrogenase (MCAD) deficiency, ornithine transcarbamylase (OTC) deficiency, cancer caused by hepatitis B virus (HBV), etc.

In the previous study (Hae Ryung Chang et al., *Gut.*, 0:1, 2014), the present inventors 1) inhibited the expression of HNF4-α using shRNA, 2) inhibited the activity of HNF4-α by adding AMPK-activating material (metformin), and 3)

induced the inhibition of the HNF4α activity using BIM5078 (U.S. Patent Application Publication No. 2010-0286220), which is known as a HNF4-α antagonist, and as a result were able to confirm a reduction in the apoptosis induction and tumorigenesis caused by a gastric cancer cell line, and the present invention aims to select an even more effective HNF4-α antagonists.

In an aspect of the present invention, 2648 and 9269 compounds were respectively prepared based on the compounds naphthofuran and myristic acid, which are known to control HNF4-α by binding specifically to the ligand binding domain of HNF4-α.

Figure 2:
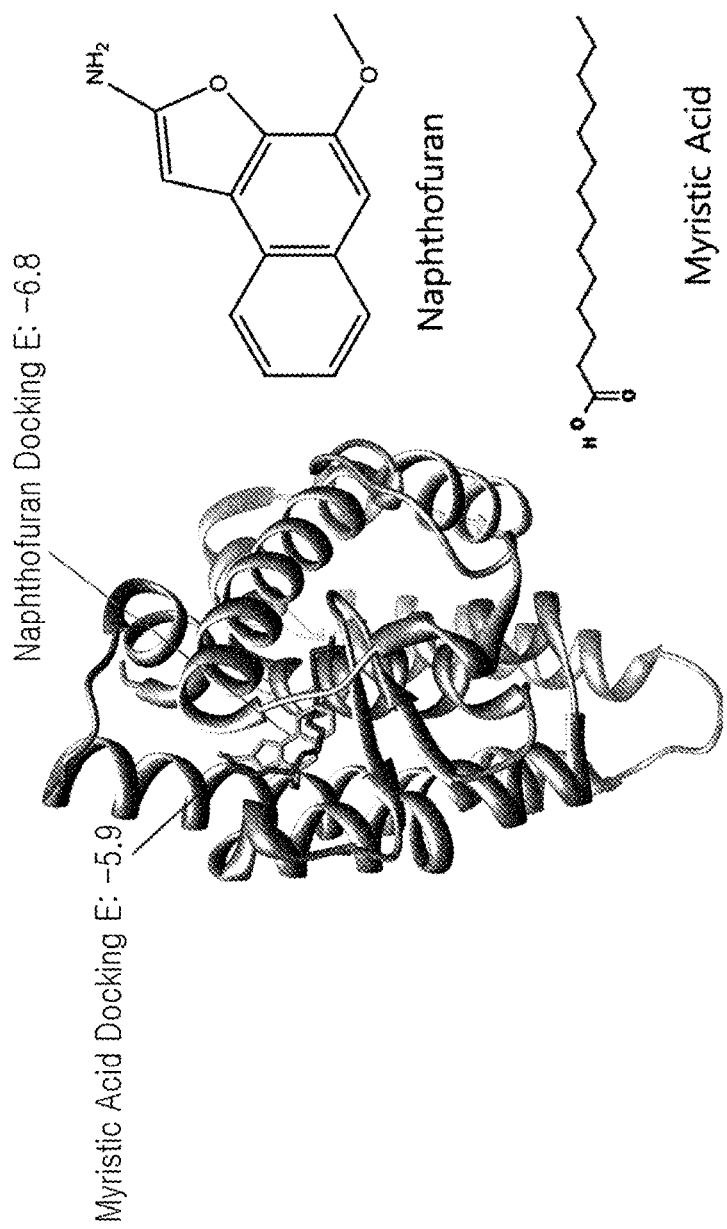
FIG. 2 is a schematic diagram illustrating the basic structures of naphthofuran and myristic acid, and a schematic diagram illustrating the feature that naphthofuran and myristic acid bind to the ligand binding domain of HNF4-α.

FIG. 2 is a schematic diagram illustrating the basic structures of naphthofuran and myristic acid, and a schematic diagram illustrating the feature that naphthofuran and myristic acid bind to the ligand binding domain of HNF4-α, and the docking energy of naphthofuran and myristic acid to the ligand binding domain of HNF4-α are −6.8 and −5.9, respectively. In the docking energy, as the "−" value becomes larger the binding becomes stronger.

In the present invention, in order to draw out materials that can specifically bind to the ligand binding domain of HNF4-α, among the compounds synthesized with naphthofuran and myristic acid as basic structures, 1 to 40 compounds were selected using computer-aided drug design (CADD) in the first selection as candidate materials of HNF4-α antagonists which can specifically bind to the ligand binding domain of HNF4-α.

As shown in Tables 2 to 5, all the compounds selected in the first selection were shown to more specifically bind to the ligand binding domain of HNF4-α, compared to naphthofuran and myristic acid, and the HNF4-α antagonists expressed by Formula 1 were drawn out based on the candidate materials 3, 4, 5, 6, 7, 10, 12, and 14, whereas the HNF4-α antagonists expressed by Formula 2 were drawn out based on the candidate materials 11, 17, and 18.

In an aspect of the present invention, the candidate material 3 expressed by Formula 3 and the candidate material 11 expressed by Formula 4 were selected with priority among the candidate materials selected in the first selection, and a binding simulation was performed on them with 4IQR, which is a HNF4-α registered on Protein Data Bank (PDB, http://www.wwpdb.org/) along with the BIM5078 (U.S. Patent Application Publication No. 2010-0286220), which is known as a HNF4-α antagonist.

Figure 3:
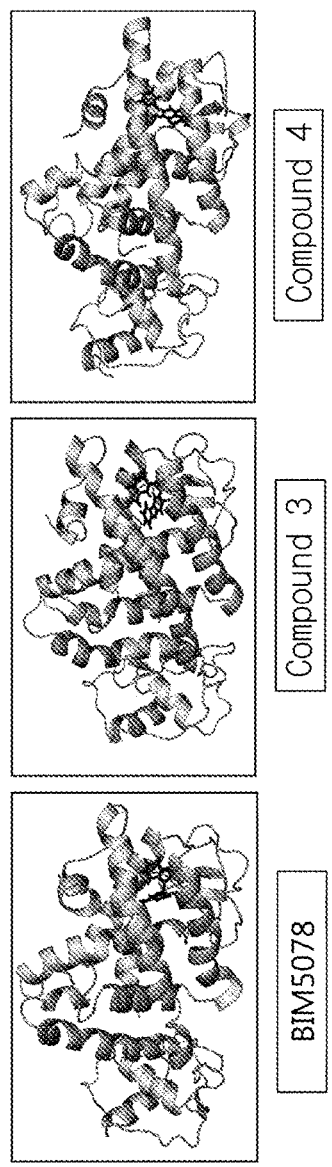
FIG. 3 is data simulating the features of the compounds expressed by Formula 3 and Formula 4, which are HNF4-α antagonists, and the feature in which the BIM5078, which was used as a positive control, was bound to the ligand binding domain of HNF4-α.

FIG. 3 is data simulating the features of the compounds expressed by Formula 3 and Formula 4, which are HNF4-α antagonists, and the feature in which the BIM5078, which was used as a positive control, was bound to the ligand binding domain of HNF4-α, and it was confirmed that the compounds expressed by Formula 3 and Formula 4 of the present invention can be bound to the ligand binding domain of HNF4-α, thus indicating that these compounds can be used as HNF4-α antagonists.

Figure 4:
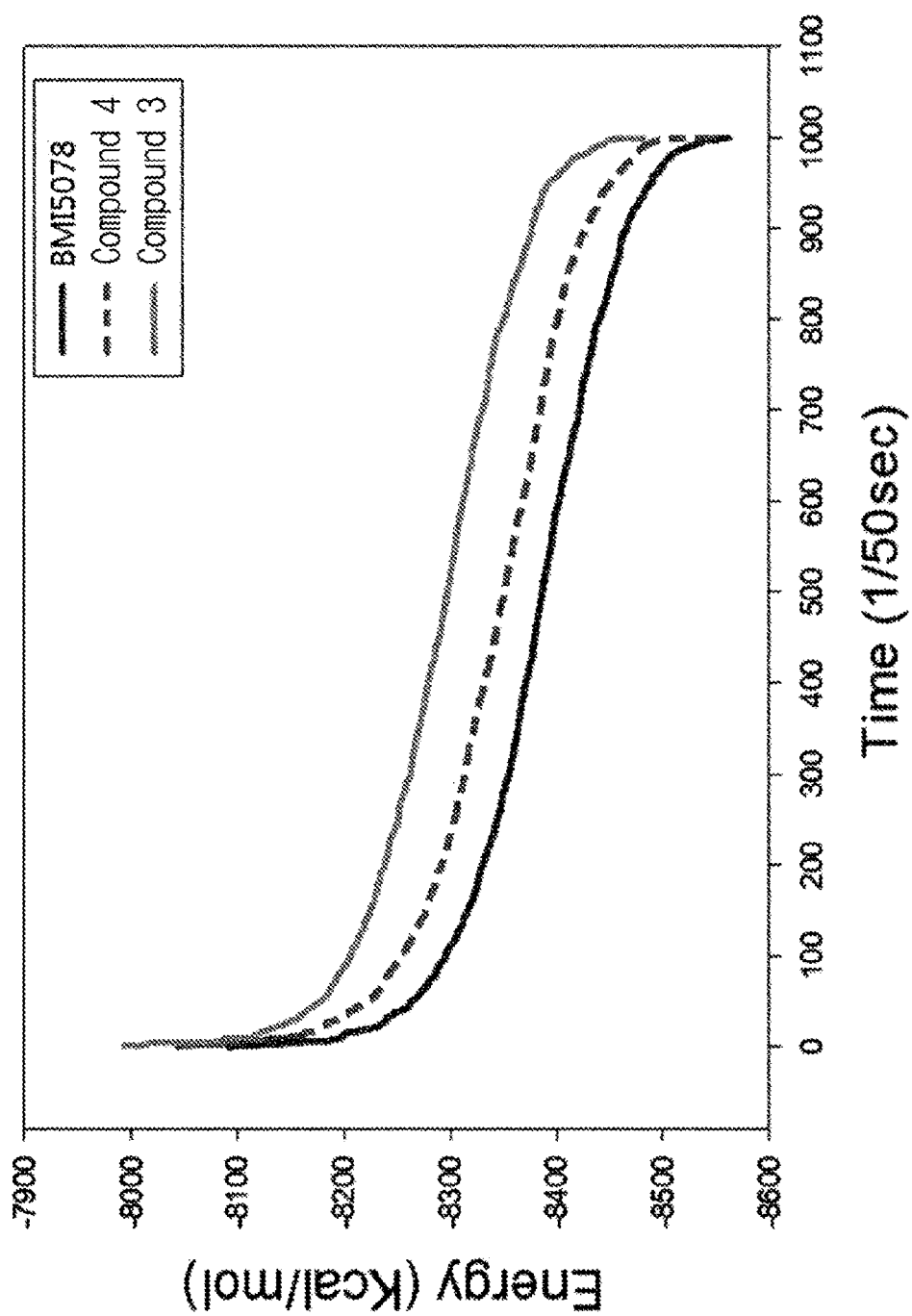
FIG. 4 is data illustrating the changes in energy when the compounds expressed by Formula 3 and Formula 4, which are HNF4-α antagonists, and the BIM5078, which was used as a positive control, are bound to the ligand binding domain of HNF4-α.

Additionally, the changes in energy when these compounds were bound to the ligand binding domain of HNF4-α were measured, and as a result, it was confirmed that these compounds exhibit an excellent binding capability compared to the BIM5078, which was used as a positive control, as shown in FIG. 4.

The present invention also provides a hepatocyte nuclear factor 4 alpha (HNF4-α) antagonist including at least one type selected from the group consisting of at least one type of a compound selected from the group consisting of the following Formula 5 and Formulas 5-1 to 5-7, which are derivatives of Formula 5; and salts thereof.

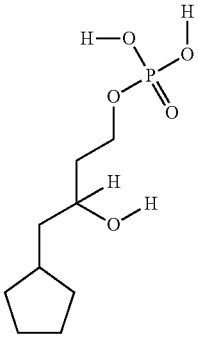

[Formula 5]

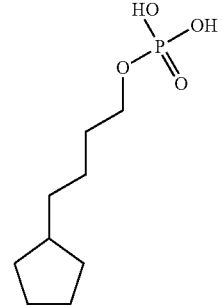

[Formula 5-1]

[Formula 5-2]

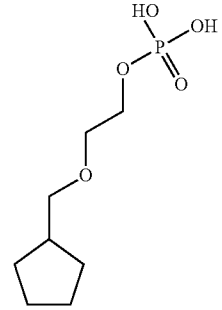

[Formula 5-3]

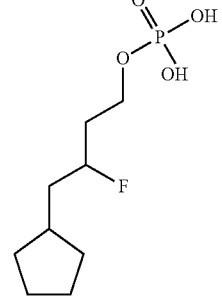

[Formula 5-4]

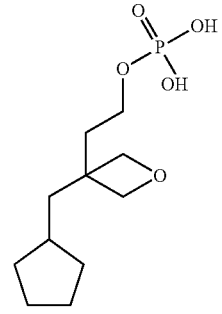

[Formula 5-5]

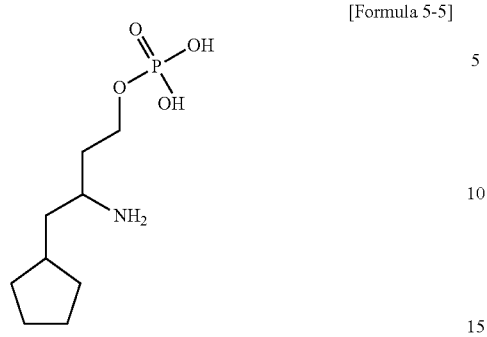

[Formula 5-6]

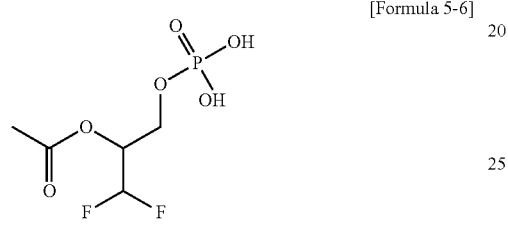

[Formula 5-7]

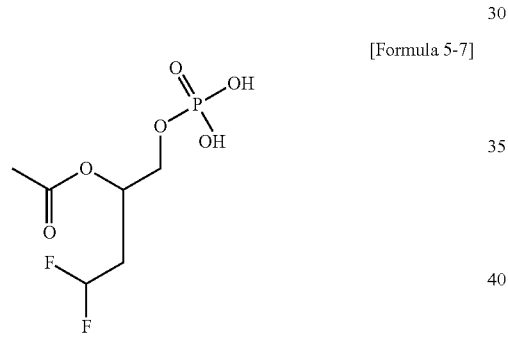

[Formula 6]

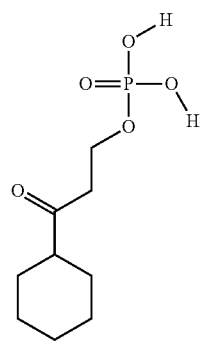

[Formula 6-1]

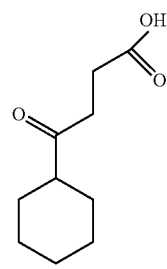

[Formula 6-2]

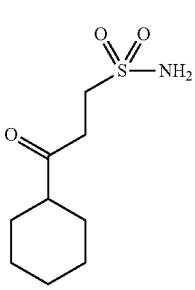

[Formula 6-3]

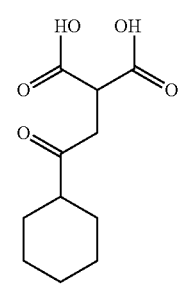

[Formula 6-4]

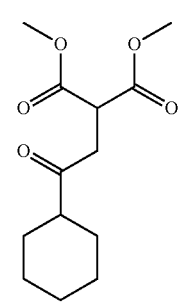

Figure 5:
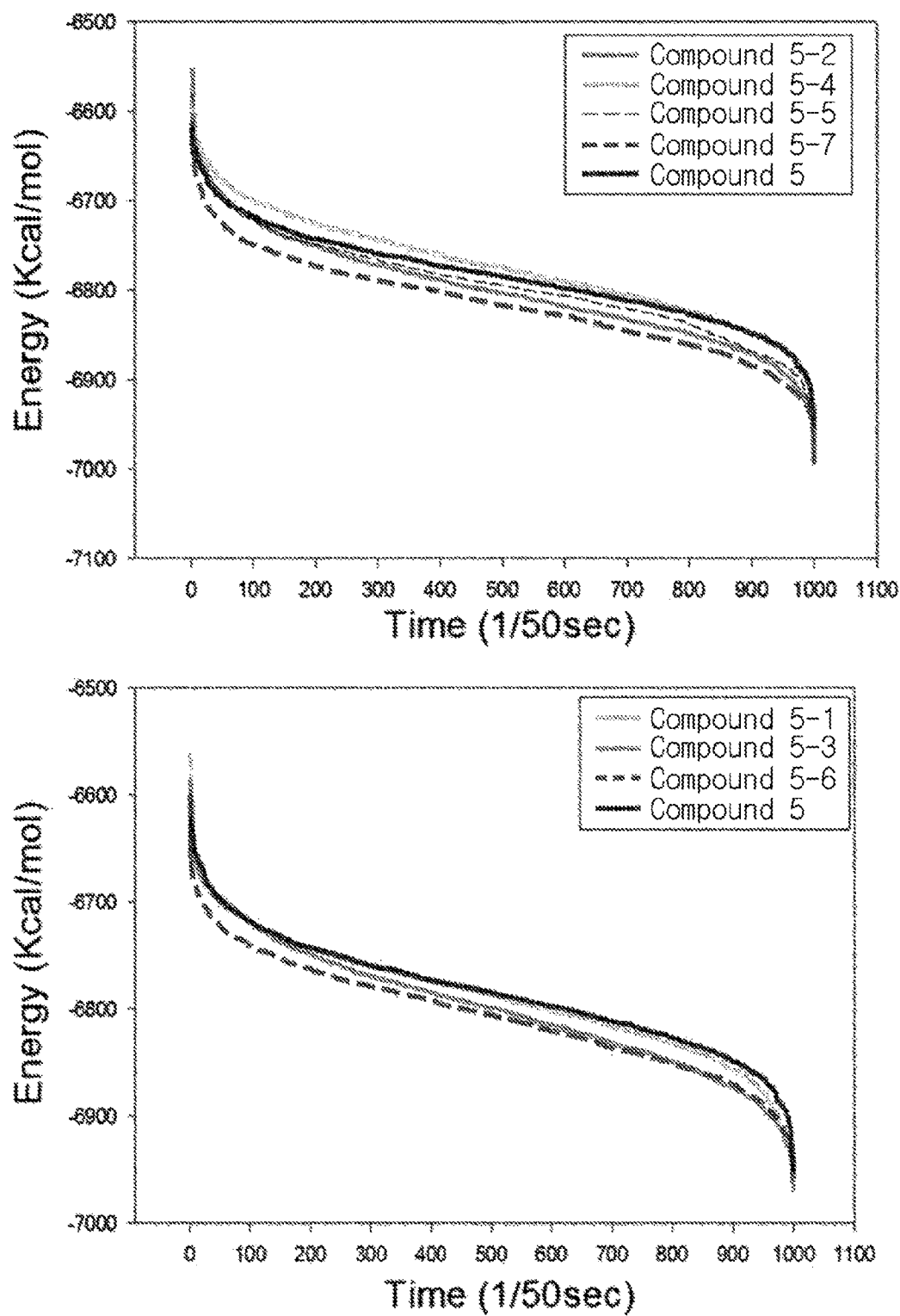
FIG. 5 is data illustrating the changes in energy when the HNF4-α antagonists expressed by Formula 5 and Formulas 5-1 to 5-7, which are derivatives of Formula 5, were bound to the ligand binding domain of HNF4-α.
Figure 6:
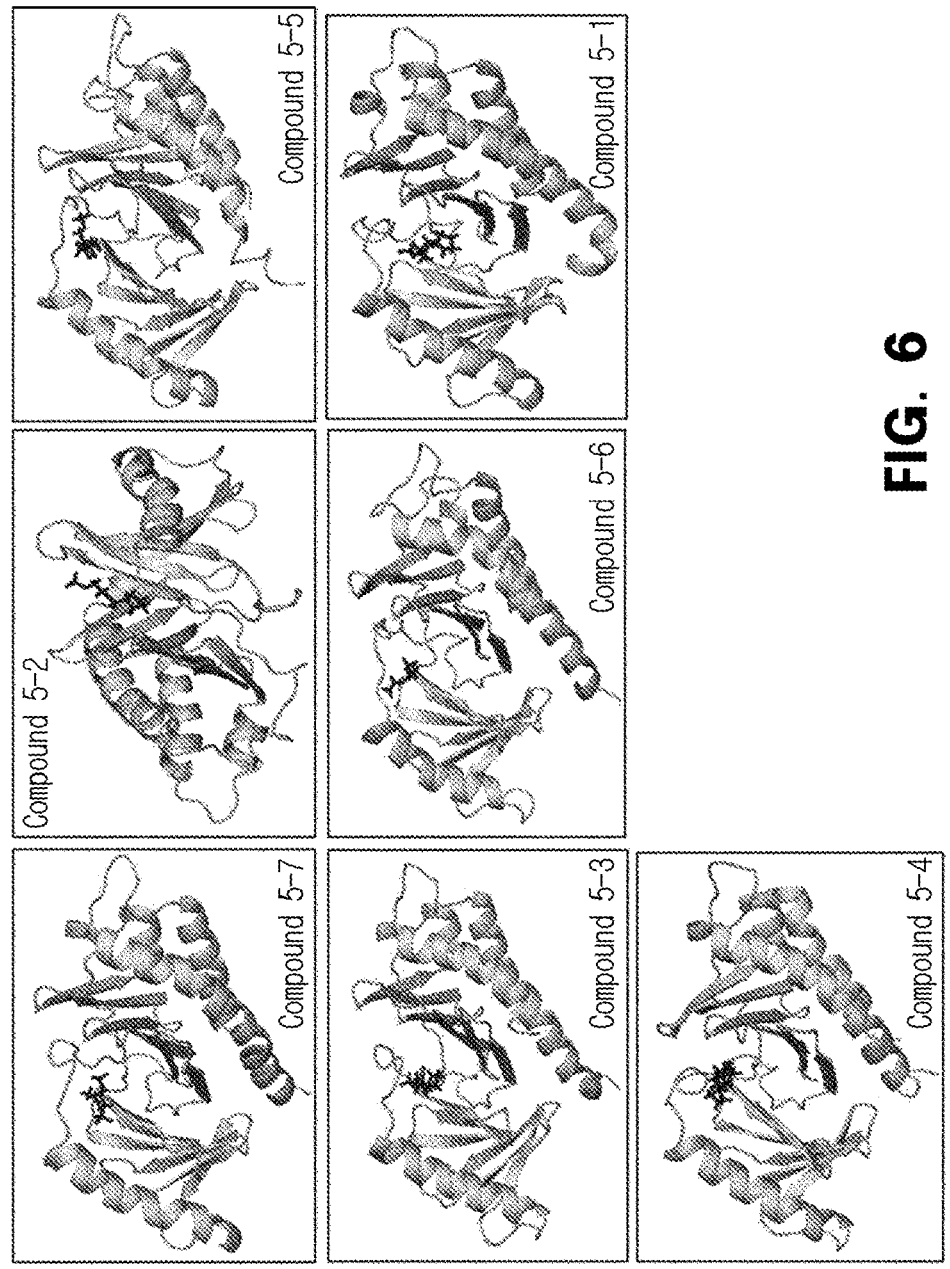
FIG. 6 is data simulating the features of the HNF4-α antagonists expressed by Formula 5 and Formulas 5-1 to 5-7, which are derivatives of Formula 5, and bound to the ligand binding domain of HNF4-α.

In an aspect of the present invention, Formula 5 and Formulas 5-1 to 5-7, which are derivatives of Formula 5, were additionally selected and synthesized. FIGS. 5 and 6 are data illustrating the changes in energy and simulating the feature when the HNF4-α antagonists expressed by Formula 5 and Formulas 5-1 to 5-7, which are derivatives of Formula 5, were bound to the ligand binding domain of HNF4-α, and the HNF4-α antagonists expressed by Formula 5 and Formulas 5-1 to 5-7, which are derivatives of Formula 5, were confirmed to specifically bind to the ligand binding domain of HNF4-α.

The present invention also provides a hepatocyte nuclear factor 4 alpha (HNF4-α) antagonist including at least one type selected from the group consisting of at least one type of a compound selected from the group consisting of the following Formula 6 and Formulas 6-1 to 6-10, which are derivatives of Formula 6; and salts thereof.

[Formula 6-5]

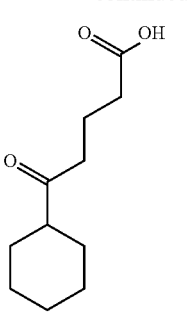

[Formula 6-6]

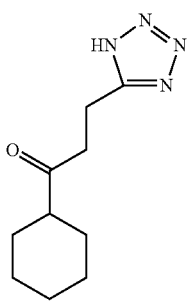

[Formula 6-7]

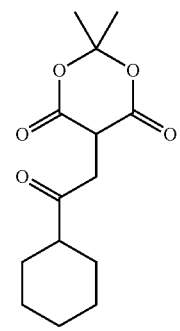

[Formula 6-8]

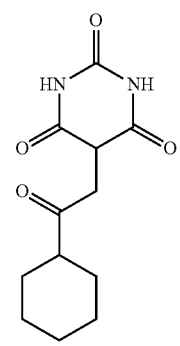

[Formula 6-9]

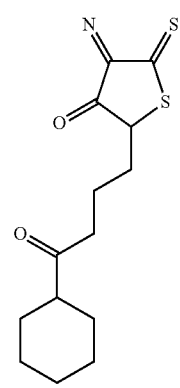

[Formula 6-10]

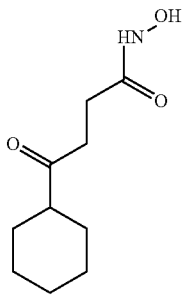

Figure 7:
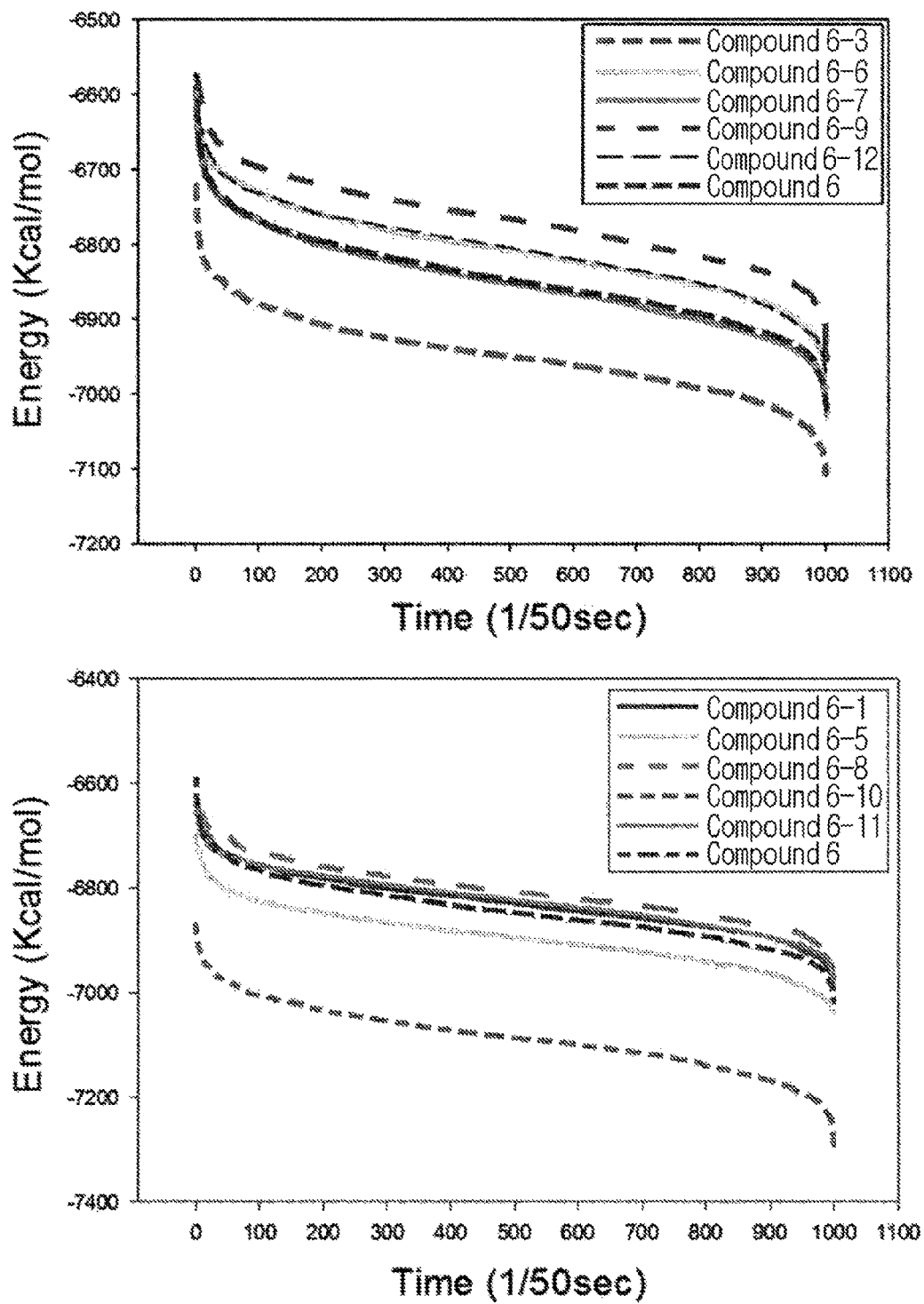
FIG. 7 is data illustrating the changes in energy when the HNF4-α antagonists expressed by Formula 6 and Formulas 6-1 to 6-10, which are derivatives of Formula 6, are bound to the ligand binding domain of HNF4-α.
Figure 8:
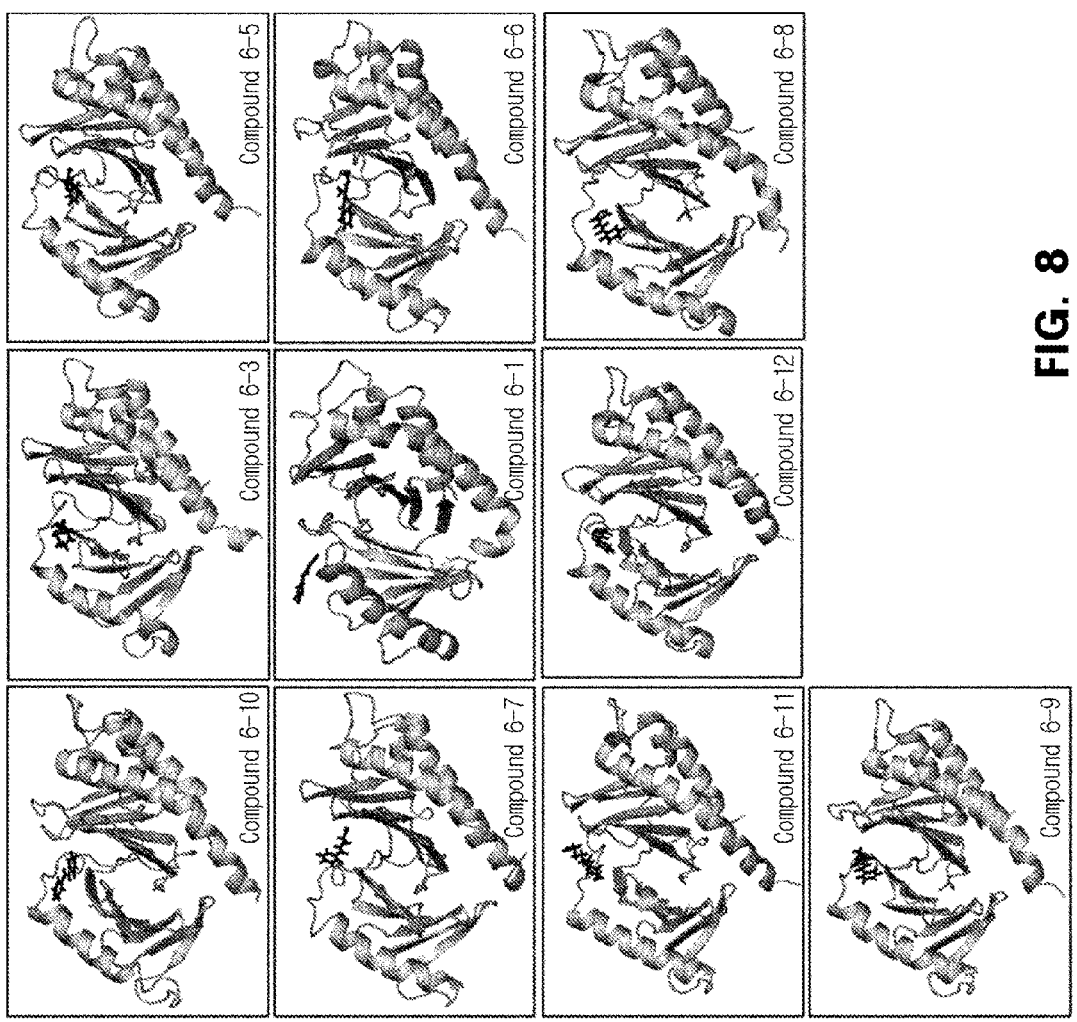
FIG. 8 is data simulating the features of the HNF4-α antagonists expressed by Formula 6 and Formulas 6-1 to 6-10, which are derivatives of Formula 6, and bound to the ligand binding domain of HNF4-α.

In an aspect of the present invention, Formula 6 and Formulas 6-1 to 6-10, which are derivatives of Formula 6, were additionally selected and synthesized. FIGS. 7 and 8 are data illustrating the changes in energy and simulating the feature when the HNF4-α antagonists expressed by Formula 6 and Formulas 6-1 to 6-10, which are derivatives of Formula 6, were bound to the ligand binding domain of HNF4-α, and the HNF4-α antagonists expressed by Formula 6 and Formulas 6-1 to 6-10, which are derivatives of Formula 6, were confirmed to specifically bind to the ligand binding domain of HNF4-α.

The present invention also provides a hepatocyte nuclear factor 4 alpha (HNF4-α) antagonist including at least one type selected from the group consisting of at least one type of a compound selected from the group consisting of the following Formula 7 and Formulas 7-1 to 7-5, which are derivatives of Formula 7; and salts thereof.

[Formula 7]

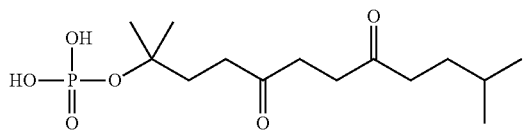

[Formula 7-1]

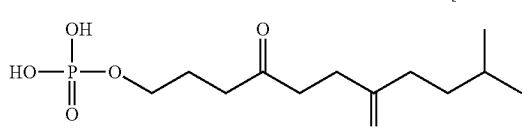

[Formula 7-2]

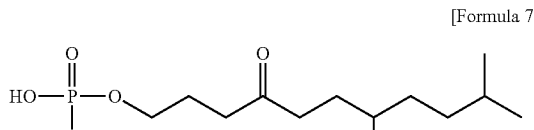

[Formula 7-3]

[Formula 7-4]

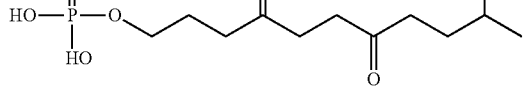

-continued

[Formula 7-5]

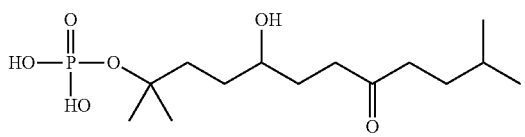

Figure 9:
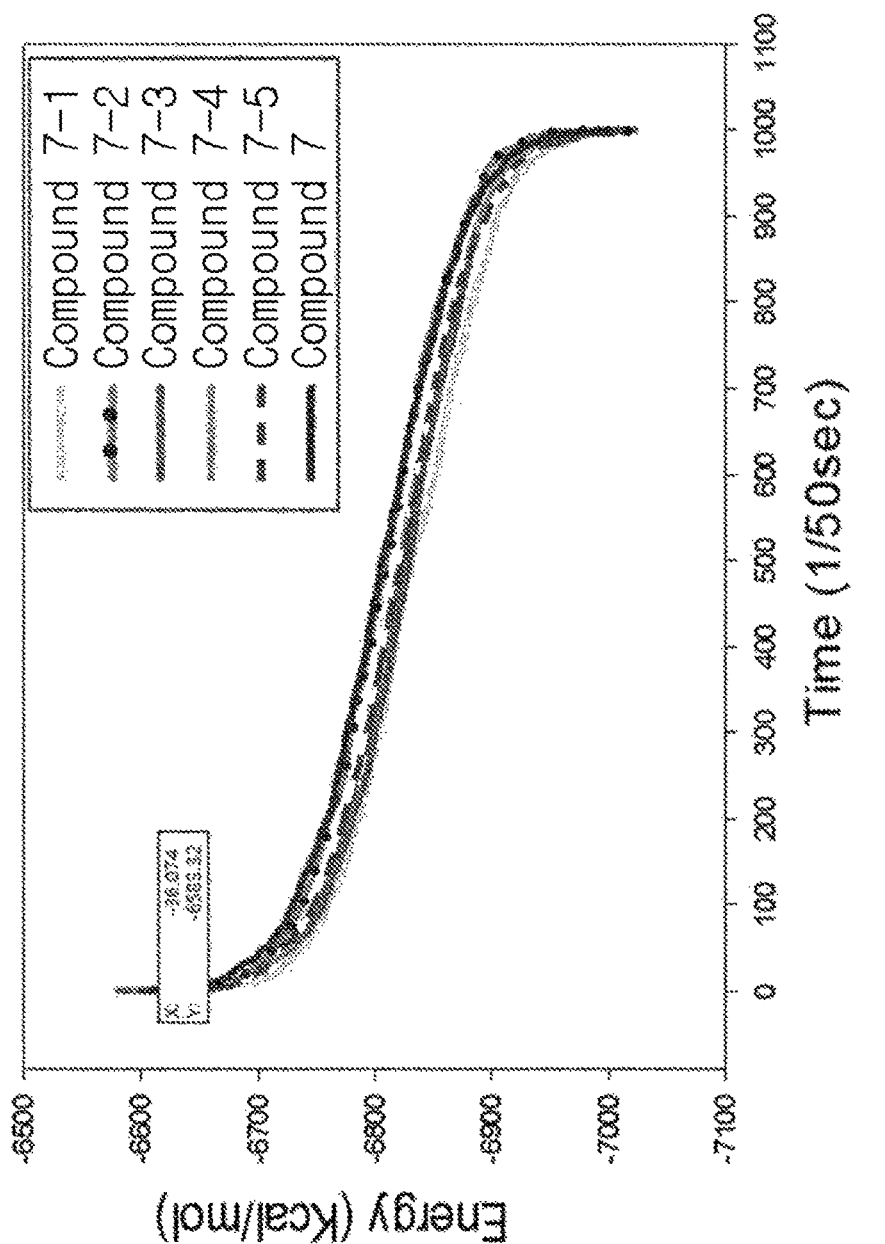
FIG. 9 is data illustrating the changes in energy when the HNF4-α antagonists expressed by Formula 7 and Formulas 7-1 to 7-5, which are derivatives of Formula 7, are bound to the ligand binding domain of HNF4-α.
Figure 10:
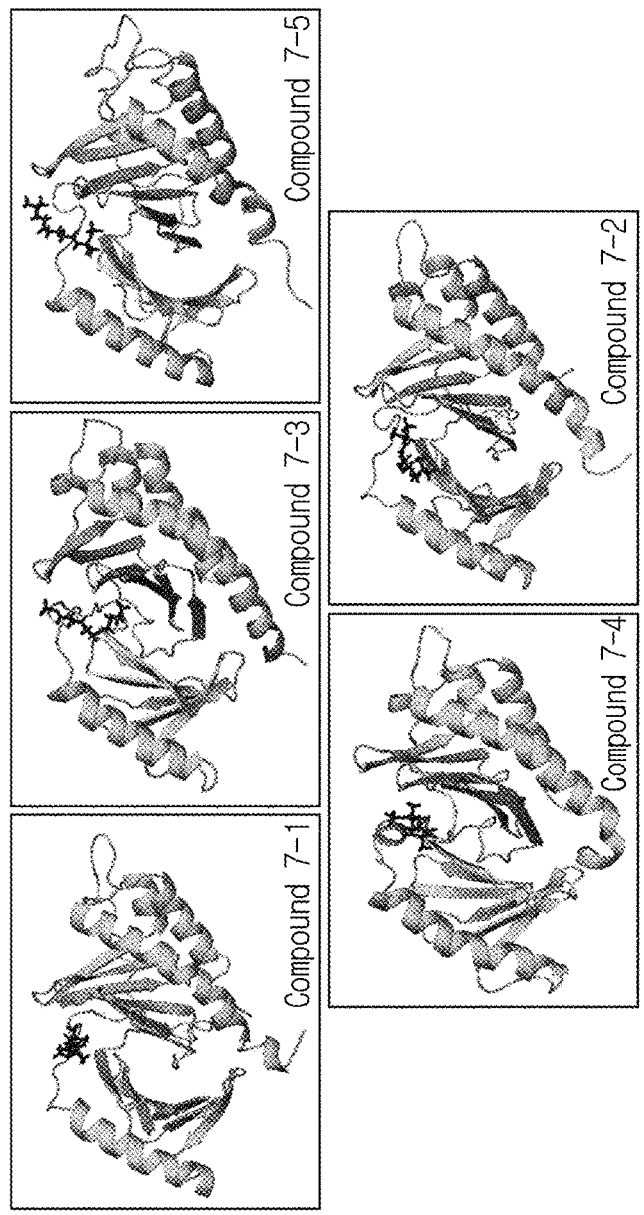
FIG. 10 is data simulating the features of the HNF4-α antagonists expressed by Formula 7 and Formulas 7-1 to 7-5, which are derivatives of Formula 7, and bound to the ligand binding domain of HNF4-α.

In an aspect of the present invention, Formula 7 and Formulas 7-1 to 7-5, which are derivatives of Formula 7, were additionally selected and synthesized. FIGS. 9 and 10 are data illustrating the changes in energy and simulating the feature when the HNF4-α antagonists expressed by Formula 7 and Formulas 7-1 to 7-5, which are derivatives of Formula 7, were bound to the ligand binding domain of HNF4-α, and the HNF4-α antagonists expressed by Formula 7 and Formulas 7-1 to 7-5, which are derivatives of Formula 7, were confirmed to specifically bind to the ligand binding domain of HNF4-α.

The present invention also provides a hepatocyte nuclear factor 4 alpha (HNF4-α) antagonist including at least one type selected from the group consisting of at least one type of a compound selected from the group consisting of the following Formula 8 and Formula 8-1, which is a derivative of Formula 8; and salts thereof.

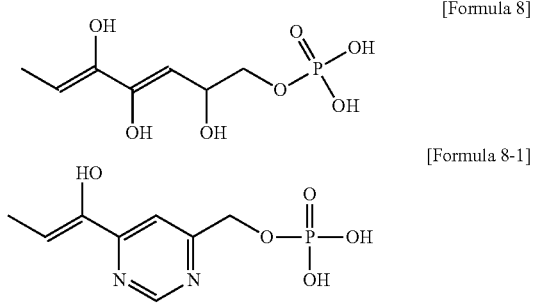

[Formula 8]

[Formula 8-1]

Figure 11:
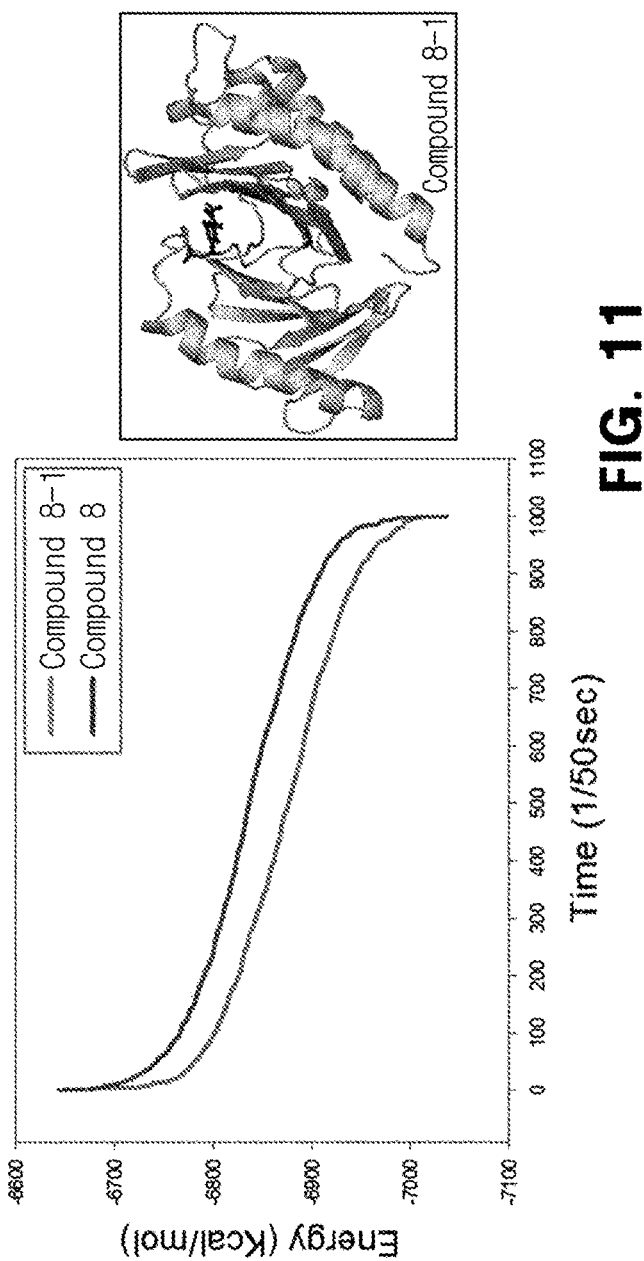
FIG. 11 is data simulating the changes in energy and the features when the HNF4-α antagonists expressed by Formula 8 and Formula 8-1, which is a derivative of Formula 8, are bound to the ligand binding domain of HNF4-α.

In an aspect of the present invention, Formula 8 and Formula 8-1, which is a derivative of Formula 8, were additionally selected and synthesized. FIG. 11 is data illustrating the changes in energy and simulating the feature when the HNF4-α antagonists expressed by Formula 8 and Formula 8-1, which is a derivative of Formula 8, were bound to the ligand binding domain of HNF4-α, and the HNF4-α antagonists expressed by Formula 8 and Formula 8-1, which is a derivative of Formula 8, were confirmed to specifically bind to the ligand binding domain of HNF4-α.

The present invention also provides a pharmaceutical composition which is for preventing and treating cancer and includes the HNF4-α antagonist as an active ingredient, and a health functional food which is for preventing and improving cancer and includes the HNF4-α antagonist as an active ingredient.

The HNF4-α antagonist can reduce the expression of wingless-type MMTV integration site family, member 5A (Wnt5a) by inhibiting the activity of HNF4-α.

Figure 12:
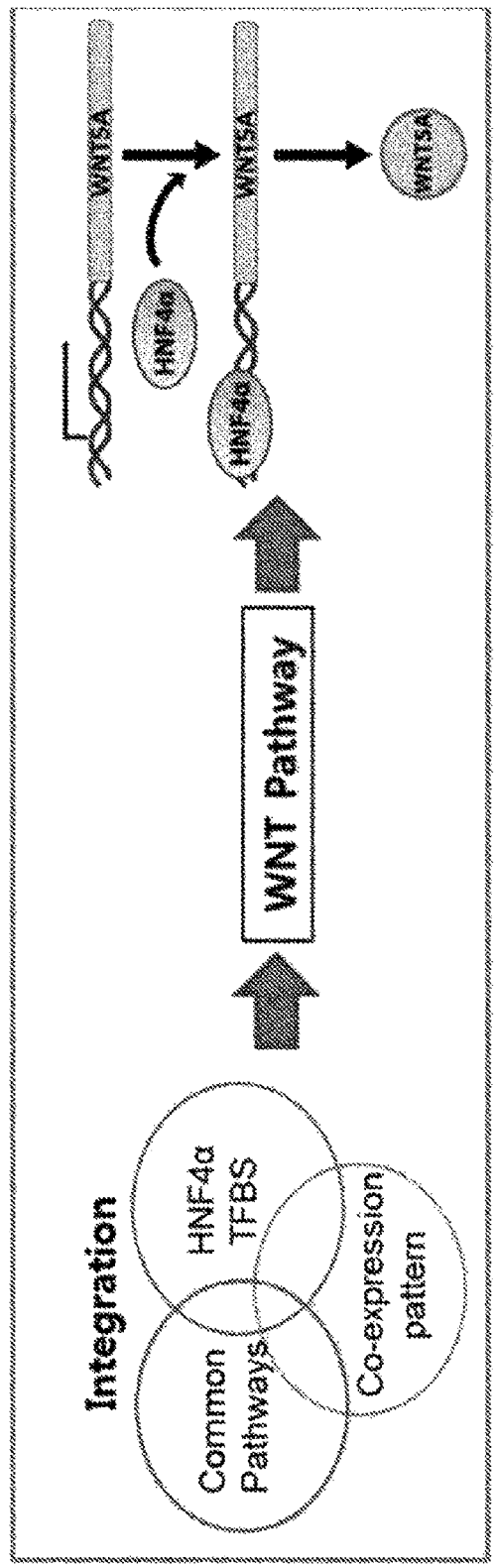
FIG. 12 is a schematic diagram illustrating the pathways of HNF4-α and WNT.

As shown in FIG. 12, HNF4-α promotes the expression of the Wnt5a gene by binding to the promoter region of the Wnt5a gene. Therefore, the HNF4-α antagonist can inhibit the binding of HNF4-α to the promoter region of the Wnt5a gene by specifically binding to the ligand binding domain of HNF4-α, and as a result, reduce the Wnt5a expression, and is thereby capable of controlling the Wnt signal.

In the present invention, the cancer may be at least one type selected from the group consisting of gastric cancer, colorectal cancer, breast cancer, cervical cancer, and liver cancer, and preferably, gastric cancer.

Figure 13:
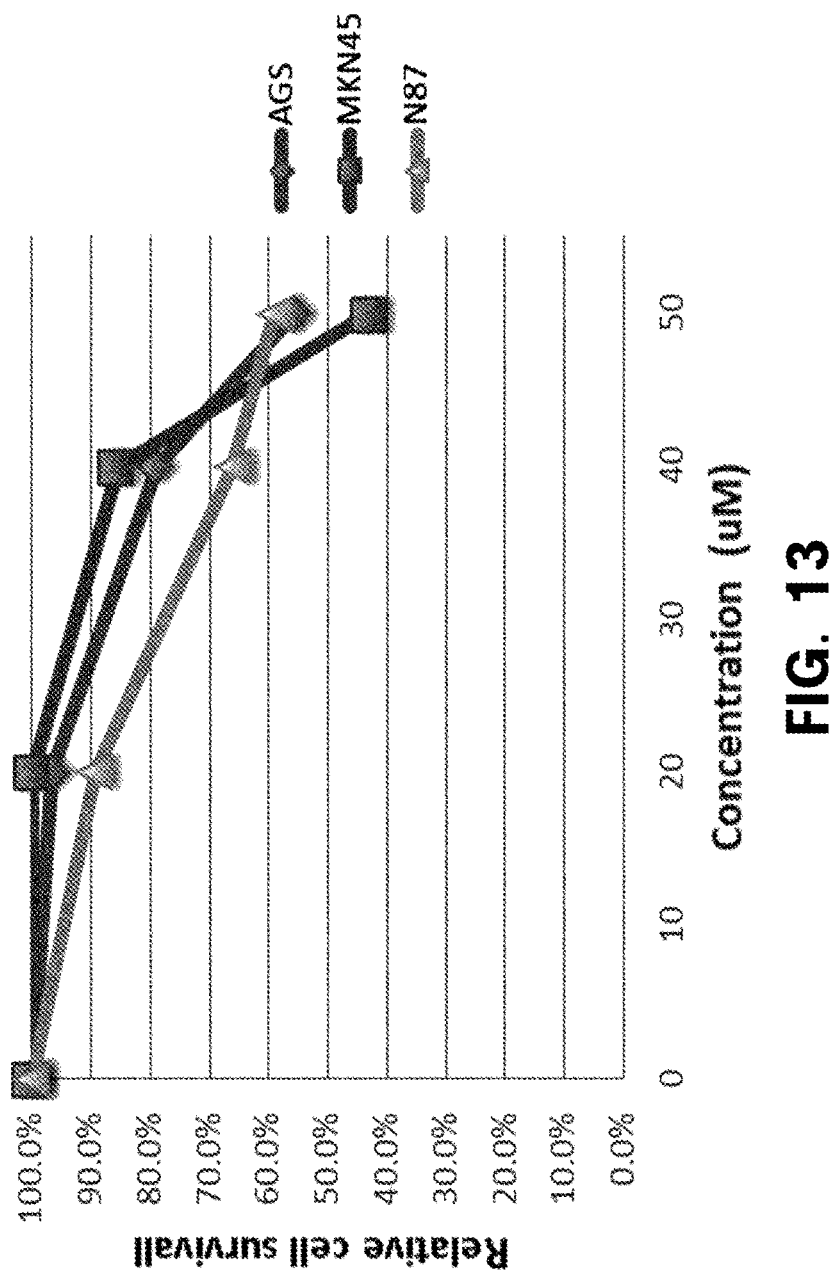
FIG. 13 is a graph illustrating the effect of cancer cell apoptosis when the compound expressed by Formula 3 was treated to a gastric cancer cell line.

As shown in FIG. 13, when a gastric cancer cell line was treated with the HNF4-α antagonist expressed by Formula 3 it effectively inhibited the growth of gastric cancer cells. The treatment induced the apoptosis of gastric cancer cells in a dose-dependent manner, and about a half of the gastric cancer cell line was apoptosized at a concentration of 50 μM, compared to the control group.

In an aspect of the present invention, various gastric cancer cell lines were treated with the HNF4-α antagonist in order to confirm whether the HNF4-α antagonist selected in the present invention can be used as a therapeutic agent for preventing or treating gastric cancer. As a result, it was confirmed that the HNF4-α antagonist treatment resulted in the inhibition or apoptosis of the gastric cancer cell lines, and also in a significant reduction of Wnt5a expression in each of the gastric cancer cells treated with the HNF4-α antagonist.

Additionally, for in vivo anticancer study, when an immunodeficient mouse was transplanted with a gastric cancer cell line into the flank to induce tumorigenesis and administered with the HNF4-α antagonist by oral administration or directly into the tumor tissues, the transplanted mouse showed a significant reduction in the size of tumor cells compared to the negative control group not treated with the HNF4-α antagonist.

Therefore, it was confirmed that the HNF4-α antagonist selected in the present invention specifically binds to the ligand binding domain of HNF4-α, and that the HNF4-α antagonist of the present invention can specifically reduce the expression of Wnt5a and inhibit the growth of gastric cancer cells compared to the existing HNF4-α antagonists, thus being applicable to a pharmaceutical composition or a health functional food for preventing and treating gastric cancer.

Additionally, the HNF4-α antagonist selected in the present invention may be applicable to a composition for treating or preventing diseases that may occur due to the overexpression of HNF4-α.

The HNF4-α antagonist selected in the present invention may be used for the preparation of a therapeutic agent for treating cancer. The HNF4-α antagonist selected in the present invention is characterized in that it enables the expression of wingless-type MMTV integration site family, member 5A (Wnt5a) by inhibiting the activity of HNF4-α.

The cancer may be at least one type selected from the group consisting of gastric cancer, colorectal cancer, breast cancer, cervical cancer, and liver cancer, and preferably, gastric cancer.

The present invention provides a method for treating cancer characterized in that the method includes administering to a subject in need thereof an effective amount of the HNF4-α antagonist selected in the present invention. Preferably, the HNF4-α antagonist of the present invention may be a compound expressed by Formula 1 or Formula 2, and most preferably a compound expressed by Formula 3.

The HNF4-α antagonist is characterized in that it enables the expression of wingless-type MMTV integration site family, member 5A (Wnt5a) by inhibiting the activity of HNF4-α, and the cancer may be at least one type selected from the group consisting of gastric cancer, colorectal cancer, breast cancer, cervical cancer, and liver cancer.

The HNF4-α antagonist and a pharmaceutically acceptable salt thereof may be administered via various routes including oral, transdermal, subcutaneous, intravenous, and intramuscular administrations. As used herein, the term "an effective amount" refers to an amount which exhibits the effects of treating and preventing cancer, and inhibiting cancer metastasis when administered to a subject, and the term "subject" used herein may refer to an animal, preferably, a mammal including humans, and may be cells, tissues, organs, etc., derived from the animal. The subject may be a patient in need of treatment.

Regarding the composition of the present invention, in general, an appropriate daily dose as a single dose or a divided dose required for treatment is an amount of about 0.01 mg to 750 mg/kg, preferably 0.1 mg to 100 mg, and most preferably 0.5 mg to 25 mg, however, the specific dose for each individual patient may vary depending on the particular compound, weight, sex, diet of a patient, administration time of drugs, administration method, excretion rate, combination of drugs, health conditions of a patient, age, etc.

The pharmaceutical composition for preventing or treating cancer including the HNF4-α antagonist according to the present invention, or the health functional food for preventing or improving cancer may further include other natural materials or compounds with an anticancer effect.

The pharmaceutical composition of the present invention may be administered to mammals including rats, mice, cattle, humans, etc., via various routes including oral, transdermal, subcutaneous, intravenous, and intramuscular administrations. Additionally, the pharmaceutical composition for preventing or treating cancer including the HNF4-α antagonist according to the present invention may be prepared in various formulations. The formulation may be formulated using a conventional diluent or excipient such as a filler, an extender, a binder, a humectant, a disintegrant, a surfactant, etc. Solid formulations for oral administration may include tablets, pills, powders, granules, capsules, etc., and these solid formulations may be prepared by adding at least one excipient, such as starch, sucrose, lactose, gelatin, etc., to the HNF4-α antagonist. Additionally, lubricants may be used in addition to the simple excipient. Liquid formulations for oral administration may include suspensions, liquid medicine for internal use, emulsions, syrups, etc., and various excipients such as humectants, sweeteners, fragrances, and preservatives, may be used, in addition to the simple diluents such as water and liquid paraffin. Formulations for parenteral administration may include sterile aqueous solutions, non-aqueous solvents, suspensions, emulsions, lyophilized formulations, suppositories, etc. Examples of the non-aqueous solvents and suspensions may include propylene glycol, polyethylene glycol, and a vegetable oil such as olive oil, an injectable ester such as ethyloleate, etc. Examples of bases for suppositories may include glycerol, gelatin, etc.

The dose of the pharmaceutical composition may be variably applied according to the age, sex, health conditions of a subject, in vivo absorption rate of active ingredients, inactive rate, excretion rate, and drugs used in combination.

Furthermore, the kind of the health functional food which is for preventing and improving cancer and includes the HNF4-α antagonist as an active ingredient may not be particularly limited, and may be, for example, meats, sausages, bread, chocolates, candies, snacks, cookies, pizzas, ramen, other noodles, gums, dairy products including ice cream, various kinds of soups, beverages, teas, drinks, alcoholic beverages, vitamin complexes, etc.

The health functional food may be used along with other foods or food additives in addition to the HNF4-α antagonist, and may be appropriately used according to the conventional method. For example, the beverages which are for preventing and treating cancer and include the HNF4-α antagonist as an active ingredient may be prepared by adding and mixing calcium, Russian ginseng concentrate, liquid fructose, distilled water, etc., in addition to the HNF4-α as an active ingredient, filling them into a drinking bottle, sterilizing, and cooling to room temperature. Additionally, a health supplement which is for preventing and improving cancer and includes the HNF4-α antagonist as an active ingredient may be prepared by adding and mixing nutrient supplementary components (vitamins B1, B2, B5, B6, and E and acetic acid ester, and nicotinic acid amide), oligosaccharides, 50% ethanol, and distilled water to the HNF4-α antagonist to form a granular phase, drying in a dryer under vacuum, passing through a 12 to 14 mesh to prepare uniform granules, and subjecting an adequate amount of the obtained granules to extrusion molding to prepare tablets or powders, or filling them into soft capsules to prepare soft capsule products.

The effective dose of the HNF4-α antagonist contained in the health food may based on the effective dose of the pharmaceutical composition, and the combined amount of active ingredients may be appropriately determined according to the purpose of use, such as preventive or therapeutic treatment. In the case of a long-term intake for the purpose of health and sanitation or health control, the dose may be less than the above range.

Hereinafter, the present invention will be described in more detail with reference to preferred embodiments such as to be easily implemented by one with ordinary skill in the art. However, the present invention may be embodied in various forms and is not limited to the Examples set forth herein.

[Example 1] Synthesis of a Material Capable of Binding to the Ligand Binding Domain of HNF4-α and Selection of Candidate Materials of HNF4-α Antagonist In the present invention, compounds having a chemical structure similar to those of naphthofuran and myristic acid, which are known to control HNF4-α by binding to the ligand binding domain of HNF4-α, were selected from pubchem (a database with a storage of 46 million compounds), and the compounds having a Tanimoto score (which is used for the selection of similarity of chemical structures) greater than 0.4 were selected. As a result of the selection, 2648 compounds and 9269 compounds, which have chemical structures similar to those of naphthofuran and myristic acid, respectively, were selected.

Materials that can specifically bind to the ligand binding domain of HNF4-α were drawn from the compounds synthesized with naphthofuran and myristic acid as basic structures, using computer-aided drug design (CADD). The docking energy for each of the compounds was measured by performing a simulation of binding with 3FS1, which is the HNF4-α registered on the Protein Data Bank (PDB, http://www.wwpdb.org/), according to the manual.

As shown in FIG. 2, due to the similarity in basic chemical structure to naphthofuran and myristic acid, the compounds can bind to the ligand binding domain of HNF4-α, and the docking energy of naphthofuran and myristic acid to HNF4-α was −6.8 and −5.9, respectively. A lower docking energy means that compounds can more stably bind to the ligand binding domain of HNF4-α.

In the main filtering, the compounds were selected which showed lower energy than those of naphthofuran and myristic acid and similar energy values to that of the BIM5078 (U.S. Pat. Application Publication No. 2010-0286220), which is a known HNF4-α antagonist, and had a size smaller than myristic acid but similar to that of the BIM5078.

Additionally, in the second filtering, the compounds complying with the conditions listed in Table 1 were selected.

TABLE 1

Conditions for selecting HNF4-α antagonist candidate materials

| Conditions | Range |
| --- | --- |
| Partition coefficient (logP) | −0.4 to +5.6 |
| Molar refractivity | 40 to 130 |
| Molecular weight | 180 to 500 |
| Number of atoms | 20 to 70 (including explicit H) |
| Polar surface area | <=140 Å2 |
| Rotatable bond (dihedral angle) | 10 or fewer |

The selected candidate materials 1 to 20 had naphthofuran as a basic structure, and the selected candidate materials 21 to 40 had myristic acid as a basic structure.

TABLE 2

HNF4-α antagonist candidate materials 1 to 10

| | Structure (CID) | Lowest E |
| --- | --- | --- |
| 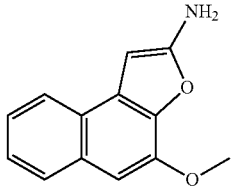 [SMILES: COc1cc2ccccc2c2cc(N)oc12] | Naphtho-furan | −6.8 |
| 1 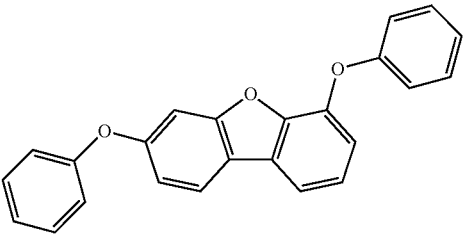 [SMILES: c1ccc(Oc2ccc3c(c2)oc2c(Oc4ccccc4)cccc23)cc1] | 23055118 | −11.00 |
| 2  | 23345854 | −11.00 |
| 3 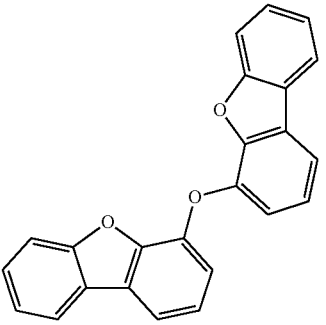 [SMILES: c1ccc2c(c1)oc1c(Oc3cccc4c3oc3ccccc34)cccc12] | 3649084 | −10.40 |

TABLE 2-continued
HNF4-α antagonist candidate materials 1 to 10
| | | Structure (CID) | Lowest E |
|---|---|---|---|
| 4 | 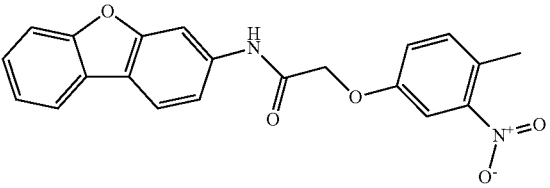 [SMILES: Cc1ccc(OCC(=O)Nc2ccc3c(c2)oc2ccccc23)cc1[N+](=O)[O-]] | 2943931 | −10.30 |
| 5 | 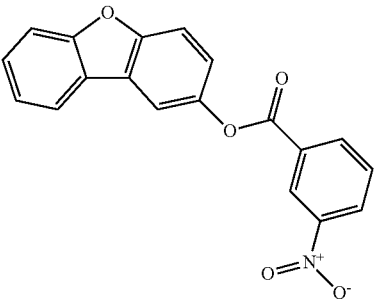 [SMILES: O=C(Oc1ccc2oc3ccccc3c2c1)c1cccc([N+](=O)[O-])c1] | 3904673 | −10.30 |
| 6 | 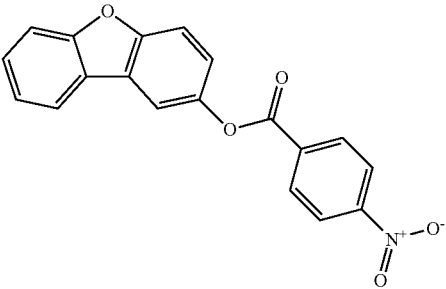 [SMILES: O=C(Oc1ccc2oc3ccccc3c2c1)c1ccc([N+](=O)[O-])cc1] | 2404390 | −10.00 |
| 7 | 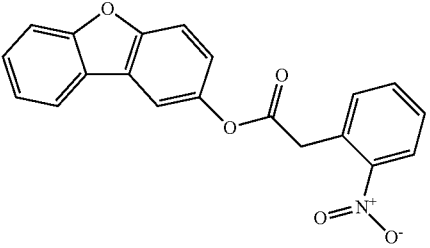 [SMILES: O=C(Cc1ccccc1[N+](=O)[O-])Oc1ccc2oc3ccccc3c2c1] | 35728809 | −10.00 |
| 8 | 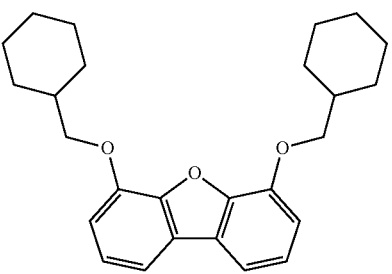 [SMILES: c1cc(OCC2CCCCC2)c2oc3c(OCC4CCCCC4)cccc3c2c1] | 66661464 | −10.00 |

TABLE 2-continued

HNF4-α antagonist candidate materials 1 to 10

| | Structure (CID) | Lowest E |
|---|---|---|
| 9 | 7935304 | −10.00 |
| 10 | 3282588 | −9.90 |

TABLE 3

HNF4-α antagonist candidate materials 11 to 20

| | Structure (CID) | Lowest E |
|---|---|---|
| 11 | 2089313 | −9.80 |
| 12 | 2397577 | −9.80 |

TABLE 3-continued
HNF4-α antagonist candidate materials 11 to 20
| | Structure (CID) | Lowest E |
|---|---|---|
| 13 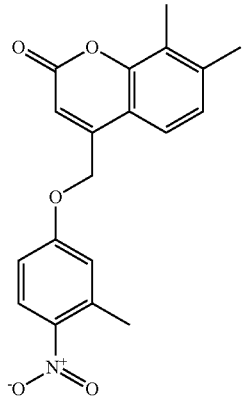 | 29617456 | −9.80 |
| 14 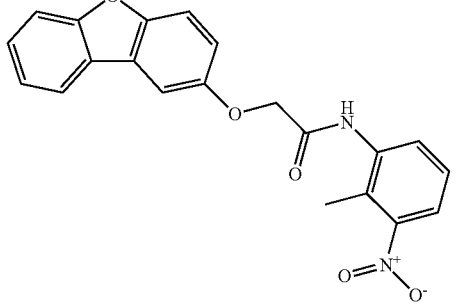 | 26796617 | −9.70 |
| 15 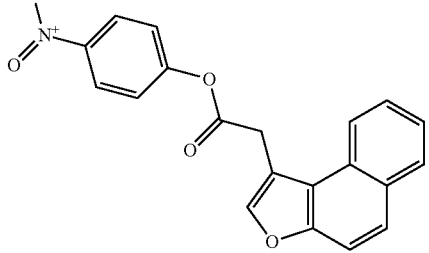 | 7900920 | −9.70 |
| 16 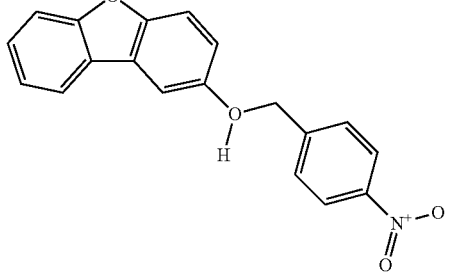 | 9839993 | −9.70 |
| 17 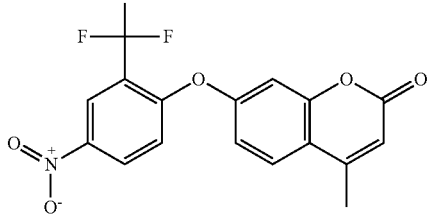 | 1323001 | −9.60 |

TABLE 3-continued
HNF4-α antagonist candidate materials 11 to 20
| | Structure (CID) | Lowest E |
|---|---|---|
| 18 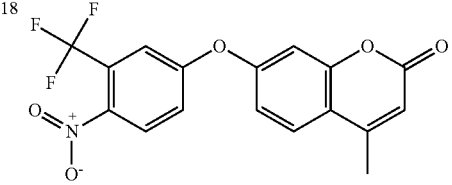 | 2087412 | −9.60 |
| 19 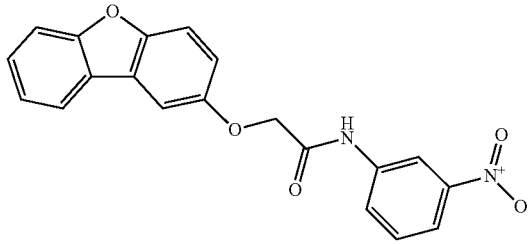 | 2438477 | −9.60 |
| 20 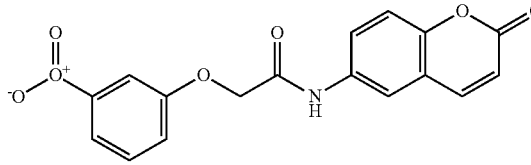 | 52368191 | −9.60 |
TABLE 4
HNF4-α antagonist candidate materials 20 to 30
| | Structure (CID) | Lowest E |
|---|---|---|
| 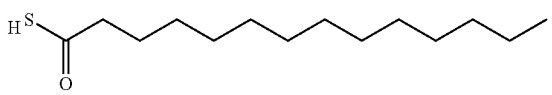 | MYR(11005) | −5.9 |
| 21 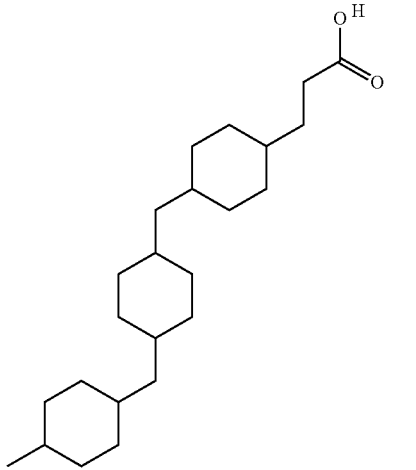 | 59048949 | −9.60 |

TABLE 4-continued
HNF4-α antagonist candidate materials 20 to 30
| | | Structure (CID) | Lowest E |
|---|---|---|---|
| 22 | 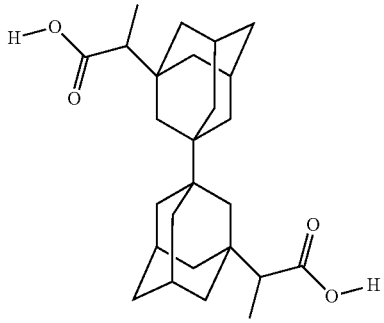 [SMILES: CC(C(=O)O)C12CC3CC(C1)CC(C14CC5CC(CC(C(C)C(=O)O)(C5)C1)C4)(C3)C2] | 22660511 | −9.50 |
| 23 | 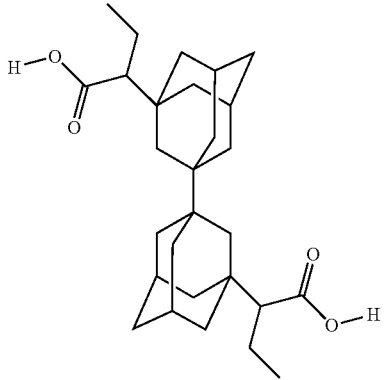 [SMILES: CCC(C(=O)O)C12CC3CC(C1)CC(C14CC5CC(CC(C(CC)C(=O)O)(C5)C1)C4)(C3)C2] | 22660512 | −9.50 |
| 24 | 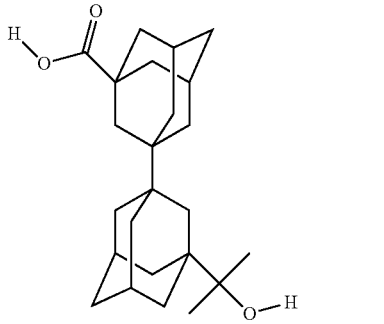 [SMILES: CC(C)(O)C12CC3CC(C1)CC(C14CC5CC(CC(C(=O)O)(C5)C1)C4)(C3)C2] | 44625575 | −9.50 |
| 25 | 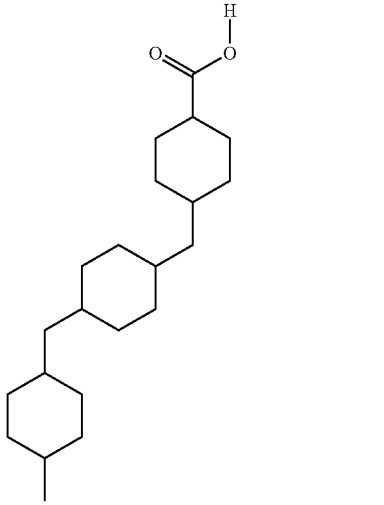 [SMILES: CC1CCC(CC2CCC(CC3CCC(C(=O)O)CC3)CC2)CC1] | 57764746 | −9.40 |

TABLE 4-continued

HNF4-α antagonist candidate materials 20 to 30

| | Structure (CID) | Lowest E |
|---|---|---|
| 26 | 58493861 | −9.40 |
| 27 | 22660515 | −9.30 |
| 28 | 14511605 | −9.10 |
| 29 | 13280700 | −9.00 |

TABLE 4-continued

HNF4-α antagonist candidate materials 20 to 30

| | Structure (CID) | Lowest E |
|---|---|---|
| 30 | 22445971 | −9.00 |

TABLE 5

HNF4-α antagonist candidate materials 31 to 40

| | Structure (CID) | Lowest E |
|---|---|---|
| 31 | 19593543 | −8.90 |
| 32 | 21773206 | −8.90 |

TABLE 5-continued

HNF4-α antagonist candidate materials 31 to 40

| | Structure | (CID) | Lowest E |
|---|---|---|---|
| 33 | | 69919679 | −8.90 |
| 34 | | 22383158 | −8.80 |
| 35 | | 22157196 | −8.70 |

TABLE 5-continued

HNF4-α antagonist candidate materials 31 to 40

| | | Structure (CID) | Lowest E |
|---|---|---|---|
| 36 | | 53783087 | −8.70 |
| 37 | | 17764038 | −8.60 |
| 38 | | 20320744 | −8.60 |

TABLE 5-continued

HNF4-α antagonist candidate materials 31 to 40

| | Structure (CID) | Lowest E |
|---|---|---|
| 39 | 44625744 | −8.60 |
| 40 | 59582177 | −8.60 |

As shown in Tables 2 to 5, the docking energy of the compounds selected in the first selection was in the range of −11.0 kcal/mol to −9.6 kcal/mol, and it was confirmed that the compounds more stably bind to the ligand binding domain of HNF4-α compared to those of naphthofuran and myristic acid with basic structures, the HNF4-α antagonists expressed by the following Formula 1 were drawn based on the candidate materials 3, 4, 5, 6, 7, 10, 12, and 14, and the HNF4-α antagonists expressed by the following Formula 2 were drawn based on the candidate materials 11, 17, and 18.

[Formula 1]

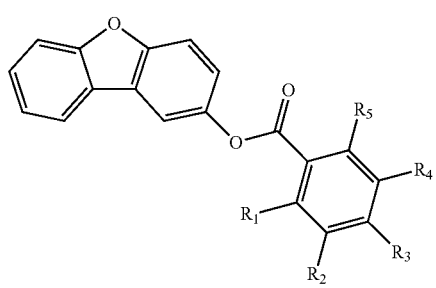

[Formula 2]

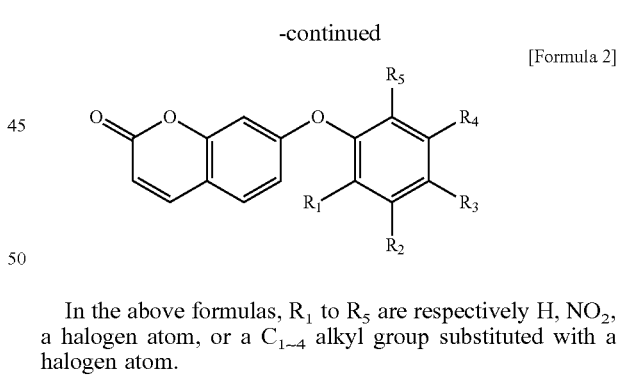

In the above formulas, $R_1$ to $R_5$ are respectively H, $NO_2$, a halogen atom, or a $C_{1-4}$ alkyl group substituted with a halogen atom.

[Example 2] Selection of HNF4-α Antagonist

In the present invention, the candidate compound 3 with the lowest docking energy expressed by the following Formula 3 and the compound 11 expressed by the following Formula 4 were selected with priority among the candidate materials selected in the first selection having naphthofuran as the basic structure, and synthesized through a request to MediGen Co., Ltd., and a binding simulation was performed of 4IQR, which is the HNF4-α registered on the Protein Data Bank (PDB, http://www.wwpdb.org/), with the BIM5078 (U.S. Patent Application Publication No. 2010-0286220), which is known as a HNF4-α antagonist.

[Formula 3]

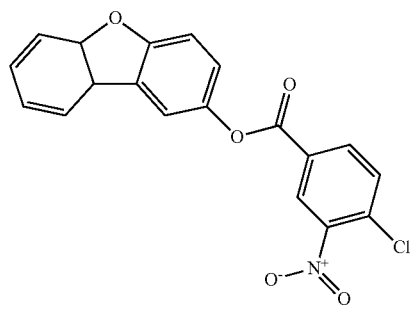

[Formula 4]

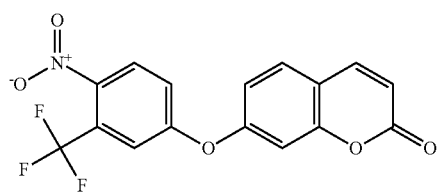

[BIM5078]

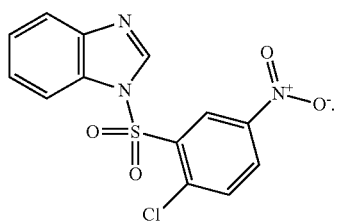

As a result, it was confirmed that the compounds of the present invention expressed by Formula 3 and Formula 4 can bind to the ligand binding domain of HNF4-α, as shown in FIG. 3. Additionally, as a result of measuring the change in docking energy when the compounds were bound to the ligand binding domain of HNF4-α, it was confirmed that that the compounds had an excellent binding capability compared to the BIM5078 which was used as a positive control, as shown in FIG. 4. These results suggest that the compounds can be used as a HNF4-α antagonist.

[Example 3] Selection of HNF4-α Antagonist and Measurement of Docking Energy with HNF4-α

In the present invention, the HNF4-α antagonists which can specifically bind to the ligand binding domain of HNF4-α were additionally selected, and the compounds expressed by the following Formulas 5 to 8 were prepared therefrom. Furthermore, the compounds expressed by the Formulas 5-1 to 5-7, which are derivatives of Formula 5; the compounds expressed by Formulas 6-1 to 6-10, which are derivatives of Formula 6; the compounds expressed by Formulas 7-1 to 7-5, which are derivatives of Formula 7; and the compound expressed by Formula 8-1, which is a derivative of Formula 8, were additionally prepared, and the docking energy for each of the compounds with HNF4-α was measured.

[Formula 5]

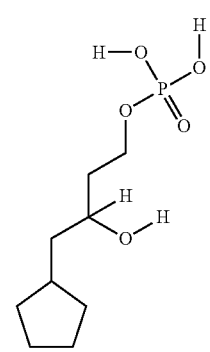

[Formula 5-1]

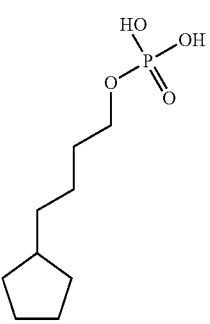

[Formula 5-2]

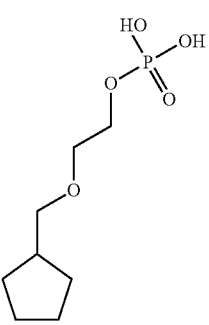

[Formula 5-3]

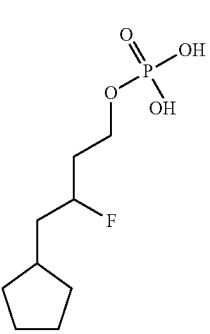

[Formula 5-4]

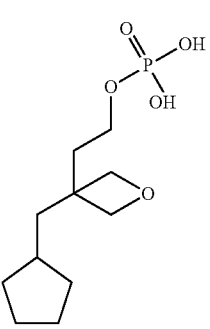

[Formula 5-5]
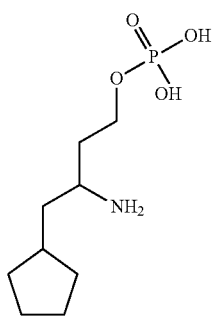
[Formula 5-6]
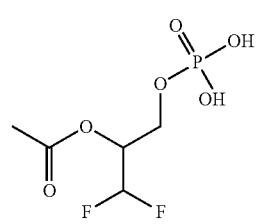
[Formula 5-7]
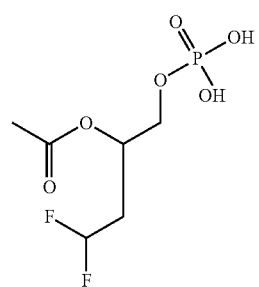
[Formula 6]
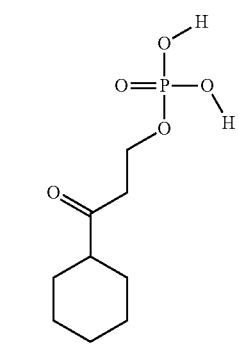
[Formula 6-1]
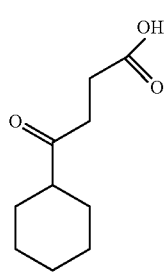
[Formula 6-2]
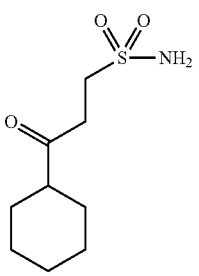
[Formula 6-3]
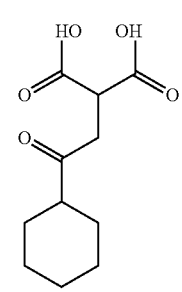
[Formula 6-4]
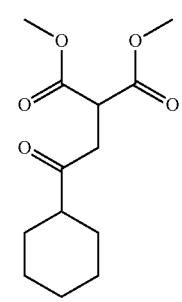
[Formula 6-5]
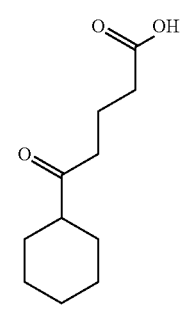
[Formula 6-6]
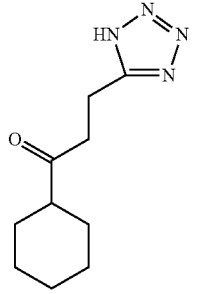

[Formula 6-7]

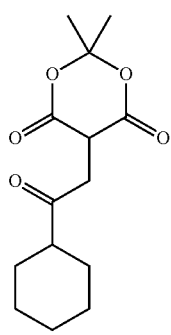

[Formula 6-8]

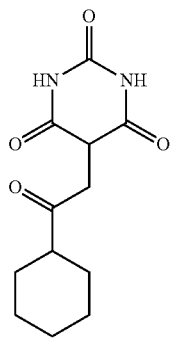

[Formula 6-9]

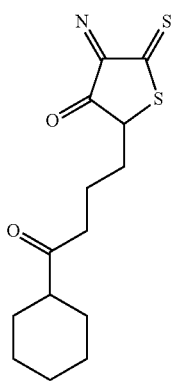

[Formula 6-10]

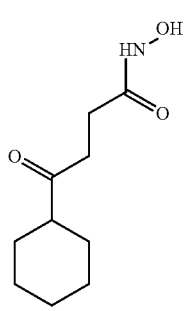

[Formula 7]

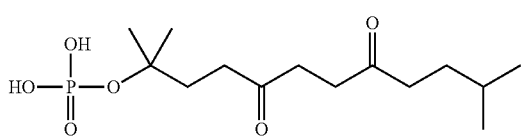

[Formula 7-1]

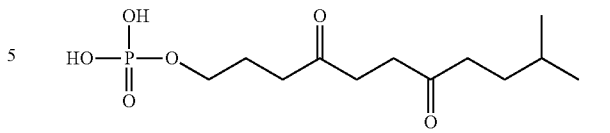

[Formula 7-2]

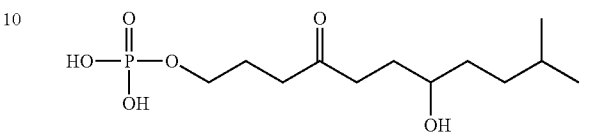

[Formula 7-3]

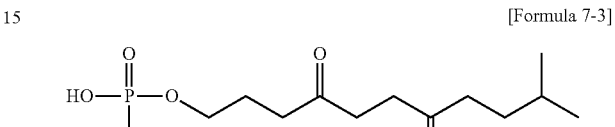

[Formula 7-4]

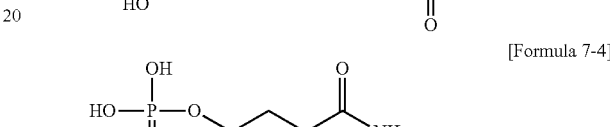

[Formula 7-5]

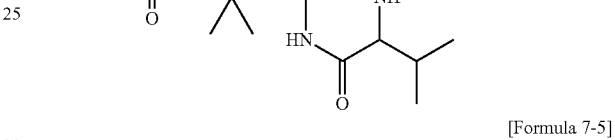

[Formula 8]

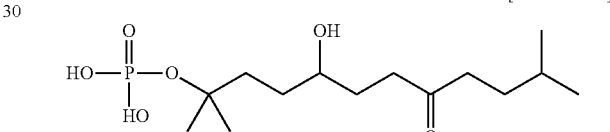

[Formula 8-1]

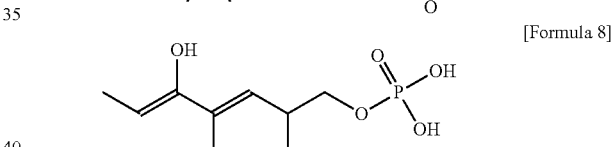

As a result, as shown in FIGS. 5 to 11, which simulate the changes in the energy and the features when the HNF4-α antagonists were bound to the ligand binding domain of HNF4-α, it was confirmed that the HNF4-α antagonists expressed by the above formulas specifically bind to the ligand binding domain of HNF4-α.

[Example 4] Synthesis of HNF4-α Antagonist

For confirmation of the apoptotic effect of compound on gastric cancer cells, the compound was synthesized. Dibenzo[b,d]furan-2-ol was purchased from Aldrich CRP and 4-chloro-3-nitrobenzoyl chloride was purchased from Medigen Co., Ltd. The two purchased compounds were mixed, treated with TEA and DMAP, and reacted for a day. The reaction scheme of the compound expressed by Formula 3 is shown in Reaction Scheme 1 below.

51

[Reaction Scheme 1]

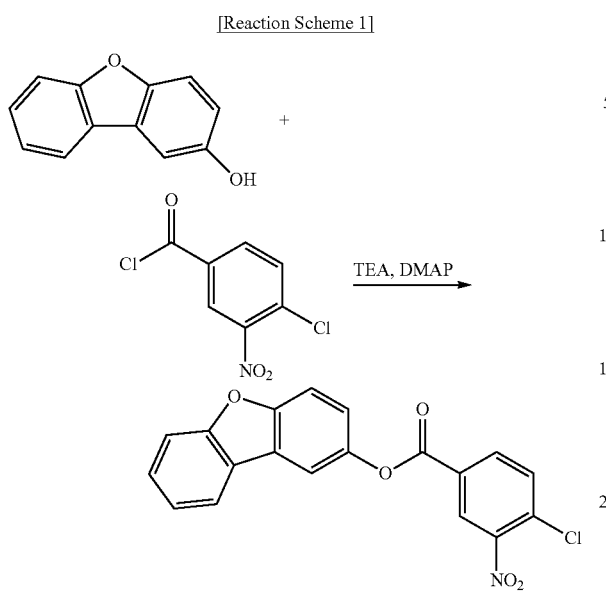

[Example 5] Apoptotic Effect on Gastric Cancer Cells

The apoptotic effect of the compound expressed by Formula 3 on gastric cancer cells was confirmed. The experiment was performed using three different kinds of gastric cancer cell lines: AGS, MKN45, and NCI-N87. Each gastric cancer cell line was grown in RPMI medium containing 10% PBS (HyClone, GE Healthcare).

Each of the gastric cancer cell lines was treated with the compound expressed by Formula 3 at concentrations of 0 μM, 20 μM, 40 μM, and 50 μM, respectively, for 48 hours. Then, the resultant was cultured in MTS assay solution for 2 hours and the survival rate of the cells was measured. MTS assay solution was used for analyzing the survival rate of the cells, and CellTiter 96® aqueous solution (Promega) was used. The experiment was performed three times in a 96-well plate.

The cell growth rate obtained in each experiment was calculated from the average value of the three experiments with the cell survival rate of the untreated negative control group set at 100%. The results are shown in FIG. 13. According to the results, the compound expressed by Formula 3 apoptosized gastric cancer cells in a dose-dependent manner. It was confirmed that the gastric cancer cell lines were apoptosized to a level of about half at 50 μM of the compound.

Accordingly, the HNF4-α antagonists selected in the present invention were confirmed to specifically bind to the ligand binding domain of HNF4-α, thereby inhibiting the activity of HNF4-α. The HNF4-α antagonists of the present invention can significantly reduce the expression of Wnt5a in a specific manner compared to that of the conventional known HNF4-α antagonists and inhibit the growth of gastric cancer cells. Therefore, the HNF4-α antagonists of the present invention can be used as a pharmaceutical composition or a health functional food for preventing and treating cancer.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

52

What is claimed is:

1. A method for inhibiting activity of hepatocyte nuclear factor 4 alpha (HNF4-α) comprising administering an effective amount of a HNF4-α antagonist comprising a compound of the following Formula 1 or salts thereof to a subject in need of inhibition of HNF4-α activity:

[Formula 1]

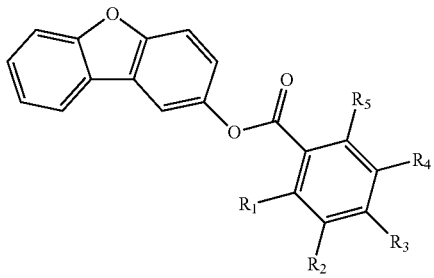

wherein $R_1$ to $R_5$ are each independently a hydrogen atom (H), a nitro group ($NO_2$), a halogen atom, a $C_{1-6}$ alkyl group substituted with one to six identical or different halogen atoms, or a $C_{1-6}$ alkyl group.

2. The method of claim 1, wherein the compound of the Formula 1 is defined by the following Formula 3:

[Formula 3]

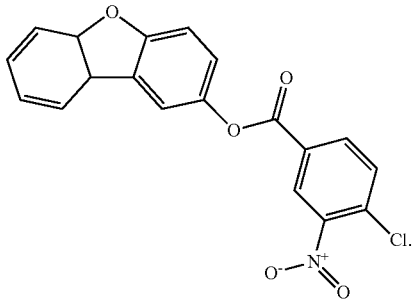

3. A method for treating gastric cancer comprising administering an effective amount of a hepatocyte nuclear factor 4 alpha (HNF4-α) antagonist comprising a compound of the following Formula 3 or salts thereof to a subject in need of gastric cancer treatment:

[Formula 3]

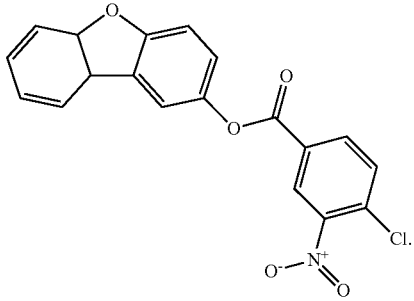

* * * * *